(12) United States Patent
Halliday et al.

(10) Patent No.: US 9,987,364 B2
(45) Date of Patent: *Jun. 5, 2018

(54) WATER-SWELLABLE POLYMERS

(71) Applicant: Ferring B.V., Hoofddorp (NL)

(72) Inventors: Janet Anne Halliday, West Lothian (GB); Jukka Tuominen, Glasgow (GB); Mark Alexander Livingstone, Irvine (GB); Frank Koppenhagen, Belmont, CA (US); Lilias Morton Currie, Blantyre (GB); Sarah Stewart, Aberdeen (GB)

(73) Assignee: Ferring B.V., Hoofddorp (NL)

( * ) Notice: Subject to any disclaimer, the term of this patent is extended or adjusted under 35 U.S.C. 154(b) by 185 days.

This patent is subject to a terminal disclaimer.

(21) Appl. No.: 14/099,663

(22) Filed: Dec. 6, 2013

(65) Prior Publication Data

US 2014/0107195 A1 Apr. 17, 2014

Related U.S. Application Data

(60) Continuation of application No. 13/571,596, filed on Aug. 10, 2012, now Pat. No. 8,628,798, which is a
(Continued)

(30) Foreign Application Priority Data

Sep. 27, 2002 (GB) .................................. 0222522.5

(51) Int. Cl.
*A61K 47/34* (2017.01)
*A61K 31/215* (2006.01)
(Continued)

(52) U.S. Cl.
CPC ................ *A61K 47/34* (2013.01); *A61K 9/02* (2013.01); *A61K 31/215* (2013.01);
(Continued)

(58) Field of Classification Search
CPC ........ A61K 31/215; A61K 47/34; A61K 9/02; C08G 18/6674; C08G 18/758; C08G 2210/00
See application file for complete search history.

(56) References Cited

U.S. PATENT DOCUMENTS 3,487,068 A 12/1969 Morozowich et al.
3,565,991 A 2/1971 Short
(Continued)

FOREIGN PATENT DOCUMENTS

DE 19842636 3/1999
DE 19742217 4/1999
(Continued)

OTHER PUBLICATIONS

Abraham, et al., "Bioresorbable poly(ester-ether urethane)s from L-lysine diisocyanate and triblock copolymers with different hydrophilic character." Journal of Biomedical Materials Research Part A (2006) 76(4): 729-736.
(Continued)

*Primary Examiner* — Aradhana Sasan
(74) *Attorney, Agent, or Firm* — Fish & Richardson P.C.

(57) ABSTRACT

A water-swellable linear polyurethane polymer is formed by reacting a polyethylene oxide (e.g. PEG 4000 to 35,000), a difunctional compound (e.g. a diamine or diol such as 1,10-decanediol) with a diisocyanate. The ratio of the three components is generally in the range 0.1-1.5 to 1 to 1.1-2.5. The polyurethane is water-swellable in the range 300 to 1700% and soluble in certain organic solvents such as dichloromethane. It can be loaded with pharmaceutically active agents, particularly of high molecular weight, to produce controlled release compositions, such as pessaries etc.

10 Claims, 8 Drawing Sheets

Related U.S. Application Data continuation of application No. 12/835,436, filed on Jul. 13, 2010, now Pat. No. 8,557,281, which is a division of application No. 10/528,875, filed as application No. PCT/GB03/04208 on Sep. 26, 2003, now abandoned.

(51) Int. Cl.
*A61K 9/02* (2006.01)
*C08G 18/75* (2006.01)
*C08G 18/66* (2006.01)

(52) U.S. Cl.
CPC ....... *C08G 18/6674* (2013.01); *C08G 18/758* (2013.01); *C08G 2210/00* (2013.01)

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,639,157 A | 2/1972 | Wunder et al. |
| 3,731,683 A | 5/1973 | Zaffaroni |
| 3,734,097 A | 5/1973 | Zaffaroni |
| 3,737,521 A | 6/1973 | Born |
| 3,760,805 A | 9/1973 | Higuchi |
| 3,797,494 A | 3/1974 | Zaffaroni |
| 3,830,907 A | 8/1974 | Short |
| 3,845,761 A | 11/1974 | Zaffaroni |
| 3,845,770 A | 11/1974 | Theeuwes et al. |
| 3,854,480 A | 12/1974 | Zaffaroni |
| 3,860,701 A | 1/1975 | Short |
| 3,867,933 A | 2/1975 | Kitrilakis |
| 3,881,043 A | 4/1975 | Rieser et al. |
| 3,892,842 A | 7/1975 | Zaffaroni |
| 3,896,819 A | 7/1975 | Zaffaroni |
| 3,901,852 A | 8/1975 | Shah |
| 3,916,898 A | 11/1975 | Robinson |
| 3,916,899 A | 11/1975 | Theeuwes et al. |
| 3,921,636 A | 11/1975 | Zaffaroni |
| 3,931,113 A | 1/1976 | Seeger et al. |
| 3,934,580 A | 1/1976 | Cournut |
| 3,941,880 A | 3/1976 | Short |
| 3,948,254 A | 4/1976 | Zaffaroni |
| 3,948,262 A | 4/1976 | Zaffaroni |
| 3,967,618 A | 7/1976 | Zaffaroni |
| 3,993,072 A | 11/1976 | Zaffaroni |
| 3,993,073 A | 11/1976 | Zaffaroni |
| 3,995,631 A | 12/1976 | Higuchi et al. |
| 4,018,918 A | 4/1977 | Ayer et al. |
| 4,034,756 A | 7/1977 | Higuchi et al. |
| 4,036,227 A | 7/1977 | Zaffaroni et al. |
| 4,036,360 A | 7/1977 | Deffeyes |
| 4,041,208 A | 8/1977 | Seeger et al. |
| 4,093,708 A | 6/1978 | Zaffaroni et al. |
| 4,096,238 A | 6/1978 | Zaffaroni et al. |
| 4,098,747 A | 7/1978 | Bailey et al. |
| 4,135,514 A | 1/1979 | Zaffaroni et al. |
| 4,142,526 A | 3/1979 | Zaffaroni et al. |
| 4,202,880 A | 5/1980 | Fildes et al. |
| 4,205,115 A | 5/1980 | Piccirilli et al. |
| 4,215,691 A | 8/1980 | Wong |
| 4,235,988 A | 11/1980 | Fildes et al. |
| 4,237,885 A | 12/1980 | Wong |
| 4,250,611 A | 2/1981 | Wong |
| 4,264,757 A | 4/1981 | Park |
| 4,276,405 A | 6/1981 | Koleske et al. |
| 4,286,587 A | 9/1981 | Wong |
| 4,289,757 A | 9/1981 | Glenn |
| 4,327,727 A | 5/1982 | Prahl et al. |
| 4,379,915 A | 4/1983 | Watanabe et al. |
| 4,402,695 A | 9/1983 | Wong |
| 4,404,296 A | 9/1983 | Schapel |
| 4,426,485 A | 1/1984 | Hoy et al. |
| 4,438,225 A | 3/1984 | Peerman |
| 4,447,591 A | 5/1984 | Watanabe et al. |
| 4,466,936 A | 8/1984 | Schapel |
| 4,503,216 A | 3/1985 | Fagerburg et al. |
| 4,568,741 A | 2/1986 | Livingston |
| 4,594,240 A | 6/1986 | Kawata et al. |
| 4,596,576 A | 6/1986 | de Nijs |
| 4,647,596 A | 3/1987 | Ishii et al. |
| 4,694,238 A | 9/1987 | Norton |
| 4,707,495 A | 11/1987 | Rosenthale et al. |
| 4,731,289 A | 3/1988 | Coleman |
| 4,767,787 A | 8/1988 | Kawata et al. |
| 4,804,691 A | 2/1989 | English et al. |
| 4,814,182 A | 3/1989 | Graham et al. |
| 4,818,517 A | 4/1989 | Kwee et al. |
| 4,894,238 A | 1/1990 | Embry et al. |
| 4,895,934 A | 1/1990 | Matier et al. |
| 4,917,686 A | 4/1990 | Bayston et al. |
| 4,931,288 A | 6/1990 | Embrey et al. |
| 4,933,418 A | 6/1990 | Sterrett |
| 4,940,588 A | 7/1990 | Sparks et al. |
| 4,945,149 A | 7/1990 | Matsumoto et al. |
| 4,952,402 A | 8/1990 | Sparks et al. |
| 4,954,043 A | 9/1990 | Yoshida et al. |
| 4,973,304 A | 11/1990 | Graham et al. |
| 5,000,955 A | 3/1991 | Gould |
| 5,002,540 A | 3/1991 | Brodman et al. |
| 5,017,382 A | 5/1991 | Embrey et al. |
| 5,023,252 A | 6/1991 | Hseih |
| 5,035,891 A | 7/1991 | Runkel et al. |
| 5,045,622 A | 9/1991 | Kohno et al. |
| 5,049,638 A | 9/1991 | Matsumoto et al. |
| 5,055,516 A | 10/1991 | Fisch et al. |
| 5,057,573 A | 10/1991 | Pascault et al. |
| 5,061,254 A | 10/1991 | Karakelle et al. |
| 5,079,009 A | 1/1992 | Embrey et al. |
| 5,100,926 A | 3/1992 | Kondo et al. |
| 5,110,598 A | 5/1992 | Kwan |
| 5,114,718 A | 5/1992 | Damani |
| 5,116,932 A | 5/1992 | Fujiwa |
| 5,118,779 A | 6/1992 | Szycher |
| 5,130,126 A | 7/1992 | Koyama et al. |
| 5,134,151 A | 7/1992 | Bartroli et al. |
| 5,156,900 A | 10/1992 | Nishimura |
| 5,159,047 A | 10/1992 | Simms |
| 5,176,907 A | 1/1993 | Leong |
| 5,178,874 A | 1/1993 | Kwan et al. |
| 5,219,663 A | 6/1993 | Kohno et al. |
| 5,219,885 A | 6/1993 | Frolich et al. |
| 5,252,602 A | 10/1993 | Alam et al. |
| 5,269,321 A | 12/1993 | MacDonald et al. |
| 5,283,297 A | 2/1994 | Miyachi et al. |
| 5,310,759 A | 5/1994 | Bockman |
| 5,312,865 A | 5/1994 | Hoefer et al. |
| 5,322,063 A | 6/1994 | Allen et al. |
| 5,324,746 A | 6/1994 | McKee et al. |
| 5,326,632 A | 7/1994 | Zenda et al. |
| 5,328,954 A | 7/1994 | Sarangapani |
| 5,354,556 A | 10/1994 | Sparks et al. |
| 5,374,704 A | 12/1994 | Muller et al. |
| 5,464,868 A | 11/1995 | Frolich et al. |
| 5,470,829 A | 11/1995 | Prisell et al. |
| 5,472,785 A | 12/1995 | Stobbie, IV et al. |
| 5,474,767 A | 12/1995 | Tremont |
| 5,505,962 A | 4/1996 | Sparks |
| 5,510,384 A | 4/1996 | McKee et al. |
| 5,514,698 A | 5/1996 | Ahmad et al. |
| 5,527,534 A | 6/1996 | Myhling |
| 5,574,102 A | 11/1996 | Tanigami et al. |
| 5,578,640 A | 11/1996 | Hanson |
| 5,578,643 A | 11/1996 | Hanson |
| 5,605,931 A | 2/1997 | Hanson |
| 5,627,254 A | 5/1997 | Oriani |
| 5,634,895 A | 6/1997 | Igo et al. |
| 5,650,171 A | 7/1997 | Quigley, Jr. et al. |
| 5,652,274 A | 7/1997 | Martin |
| 5,659,003 A | 8/1997 | Menovcik et al. |
| 5,676,939 A | 10/1997 | Tremont |
| 5,681,278 A | 10/1997 | Igo et al. |
| 5,681,850 A | 10/1997 | Frolich et al. |

(56) References Cited

U.S. PATENT DOCUMENTS

| | | |
|---|---|---|
| 5,686,425 A | 11/1997 | Lee |
| 5,693,319 A | 12/1997 | Tremont |
| 5,700,483 A | 12/1997 | Quigley, Jr. et al. |
| 5,710,215 A | 1/1998 | Abend |
| 5,716,676 A | 2/1998 | Schutze et al. |
| 5,723,552 A | 3/1998 | Menovcik et al. |
| 5,726,244 A | 3/1998 | McGee et al. |
| 5,726,274 A | 3/1998 | Menovcik et al. |
| 5,731,303 A | 3/1998 | Hsieh |
| 5,733,538 A | 3/1998 | Riffle |
| 5,739,113 A | 4/1998 | Lee |
| 5,744,550 A | 4/1998 | Menovcik et al. |
| 5,747,058 A | 5/1998 | Tipton et al. |
| 5,747,582 A | 5/1998 | Schutze et al. |
| 5,760,127 A | 6/1998 | Hammel et al. |
| 5,763,399 A | 6/1998 | Lee |
| 5,770,650 A | 6/1998 | McGee et al. |
| 5,777,048 A | 7/1998 | Ohrbom et al. |
| 5,780,049 A | 7/1998 | Deckner et al. |
| 5,792,810 A | 8/1998 | Menovcik et al. |
| 5,795,567 A | 8/1998 | Tremont |
| 5,817,343 A | 10/1998 | Burke |
| 5,827,925 A | 10/1998 | Tremont et al. |
| 5,827,930 A | 10/1998 | Ohrbom et al. |
| 5,827,931 A | 10/1998 | Menovcik et al. |
| 5,843,961 A | 12/1998 | Kock et al. |
| 5,849,803 A | 12/1998 | Kock et al. |
| 5,853,767 A | 12/1998 | Melman |
| 5,854,385 A | 12/1998 | McGee et al. |
| 5,855,906 A | 1/1999 | McClay |
| 5,872,195 A | 2/1999 | Green et al. |
| 5,877,216 A | 3/1999 | Place et al. |
| 5,886,039 A | 3/1999 | Kock et al. |
| 5,888,930 A | 3/1999 | Smith et al. |
| 5,891,915 A | 4/1999 | Wysor et al. |
| 5,897,879 A | 4/1999 | Friedman et al. |
| 5,900,433 A | 5/1999 | Igo et al. |
| 5,935,939 A | 8/1999 | Kararli et al. |
| 5,942,512 A | 8/1999 | Kock et al. |
| 5,942,545 A | 8/1999 | Samour et al. |
| 5,948,416 A | 9/1999 | Wagner et al. |
| 5,959,775 A | 9/1999 | Joseph et al. |
| 5,965,662 A | 10/1999 | Krebs et al. |
| 5,968,542 A | 10/1999 | Tipton |
| 5,972,372 A | 10/1999 | Saleh et al. |
| 5,973,002 A | 10/1999 | Frolich et al. |
| 5,977,172 A | 11/1999 | Yoshikawa et al. |
| 5,985,859 A | 11/1999 | Luo |
| 5,994,479 A | 11/1999 | Green et al. |
| 5,994,492 A | 11/1999 | Graham et al. |
| 6,008,312 A | 12/1999 | Shirasaka |
| 6,013,637 A | 1/2000 | Klein et al. |
| 6,022,554 A | 2/2000 | Lee et al. |
| 6,028,057 A | 2/2000 | Burns |
| 6,031,002 A | 2/2000 | Wysor et al. |
| 6,039,968 A | 3/2000 | Nabahi |
| 6,040,062 A | 3/2000 | McGee et al. |
| 6,043,224 A | 3/2000 | Lee et al. |
| 6,046,244 A | 4/2000 | Buyuktimkin et al. |
| 6,080,825 A | 6/2000 | Ohrbom et al. |
| 6,084,038 A | 7/2000 | Ohrbom et al. |
| 6,086,909 A | 7/2000 | Harrison et al. |
| 6,093,270 A | 7/2000 | Ferencz et al. |
| 6,103,256 A | 8/2000 | Nabahi |
| 6,103,765 A | 8/2000 | Neal |
| 6,103,852 A | 8/2000 | Shirasaka |
| 6,114,444 A | 9/2000 | Rehfuss et al. |
| 6,117,024 A | 9/2000 | Dewanjee |
| 6,117,843 A | 9/2000 | Baroody et al. |
| 6,123,963 A | 9/2000 | Kim et al. |
| 6,126,958 A | 10/2000 | Saleh et al. |
| 6,130,200 A | 10/2000 | Brodbeck et al. |
| 6,130,309 A | 10/2000 | Reich et al. |
| 6,140,453 A | 10/2000 | Barges et al. |
| 6,150,489 A | 11/2000 | Pudleiner et al. |
| 6,160,058 A | 12/2000 | Ohrbom et al. |
| 6,184,248 B1 | 2/2001 | Lee et al. |
| 6,187,756 B1 | 2/2001 | Lee et al. |
| 6,188,039 B1 | 2/2001 | Gass |
| 6,197,327 B1 | 3/2001 | Harrison et al. |
| 6,210,343 B1 | 4/2001 | Kanakaris et al. |
| 6,210,441 B1 | 4/2001 | Flodin |
| 6,221,997 B1 | 4/2001 | Woodhouse et al. |
| 6,284,836 B1 | 9/2001 | Hassel et al. |
| 6,294,550 B1 | 9/2001 | Place et al. |
| 6,303,147 B1 | 10/2001 | Gilis |
| 6,303,606 B1 | 10/2001 | Leonardi et al. |
| 6,306,841 B1 | 10/2001 | Place et al. |
| 6,323,241 B1 | 11/2001 | Yeager et al. |
| 6,328,991 B1 | 12/2001 | Myhling |
| 6,335,003 B1 | 1/2002 | Kim et al. |
| 6,346,599 B1 | 2/2002 | Goldberg et al. |
| 6,359,100 B1 | 3/2002 | Hostettler et al. |
| 6,403,665 B1 | 6/2002 | Sieker et al. |
| 6,410,595 B1 | 6/2002 | Neal |
| 6,413,536 B1 | 7/2002 | Gibson et al. |
| 6,414,027 B1 | 7/2002 | Neal |
| 6,414,028 B1 | 7/2002 | Buyuktimkin et al. |
| 6,416,779 B1 | 7/2002 | O'Augustine et al. |
| 6,420,510 B1 | 7/2002 | Kaufhold et al. |
| 6,423,788 B1 | 7/2002 | Bammel et al. |
| 6,440,568 B1 | 8/2002 | Kayanoki et al. |
| 6,469,016 B1 | 10/2002 | Place et al. |
| 6,469,055 B2 | 10/2002 | Lee et al. |
| 6,471,955 B1 | 10/2002 | Tremont et al. |
| 6,472,434 B1 | 10/2002 | Place et al. |
| 6,482,345 B1 | 11/2002 | Dewanjee |
| 6,486,207 B2 | 11/2002 | Yeager et al. |
| 6,488,953 B2 | 12/2002 | Halliday et al. |
| 6,495,157 B1 | 12/2002 | Pen et al. |
| 6,511,388 B1 | 1/2003 | Dewanjee |
| 6,512,073 B2 | 1/2003 | Gertzmann et al. |
| 6,521,164 B1 | 2/2003 | Plummer et al. |
| 6,537,970 B1 | 3/2003 | Vulpescu et al. |
| 6,543,828 B1 | 4/2003 | Gass |
| 6,545,119 B2 | 4/2003 | Kizumoto et al. |
| 6,559,184 B2 | 5/2003 | Neal |
| 6,572,874 B1 | 6/2003 | Harrison et al. |
| 6,586,553 B1 | 7/2003 | Muhlfeld et al. |
| 6,589,990 B1 | 7/2003 | Kanakaris et al. |
| 6,592,472 B2 | 7/2003 | Dewanjee |
| 6,593,313 B2 | 7/2003 | Place et al. |
| 6,593,369 B2 | 7/2003 | Neal |
| 6,607,686 B2 | 8/2003 | Dewanjee |
| 6,630,050 B1 | 10/2003 | Moeller et al. |
| 6,632,913 B2 | 10/2003 | Matsumoto et al. |
| 6,641,064 B1 | 11/2003 | Dentler et al. |
| 6,642,274 B1 | 11/2003 | Neal |
| 6,664,290 B1 | 12/2003 | Ei-Rafaey |
| 6,693,135 B2 | 2/2004 | Yeager et al. |
| 6,740,333 B2 | 5/2004 | Beckett et al. |
| 6,790,926 B1 | 9/2004 | Spijkers et al. |
| 6,794,372 B2 | 9/2004 | Del Soldato et al. |
| 6,825,234 B2 | 11/2004 | Yeager et al. |
| 6,841,574 B2 | 1/2005 | Mo et al. |
| 6,861,503 B2 | 3/2005 | Shalaby |
| 6,953,800 B2 | 10/2005 | Leonardi et al. |
| 6,992,161 B1 | 1/2006 | Kim et al. |
| 7,053,209 B1 | 5/2006 | Gibson et al. |
| 7,179,481 B2 | 2/2007 | Villanueva |
| 7,485,666 B2 | 2/2009 | Villanueva et al. |
| 7,670,606 B2 | 3/2010 | Volkmann |
| 7,717,892 B2 | 5/2010 | Bartning |
| 7,795,467 B1 | 9/2010 | Pacetti et al. |
| 7,829,112 B2 | 11/2010 | Ron et al. |
| 7,833,543 B2 | 11/2010 | Gibson et al. |
| 7,833,545 B2 | 11/2010 | Ron et al. |
| 7,838,024 B2 | 11/2010 | Ron et al. |
| 7,883,718 B2 | 2/2011 | Ron et al. |
| 7,892,163 B2 | 2/2011 | Bartning et al. |
| 8,557,281 B2* | 10/2013 | Halliday et al. ............ 424/468 |
| 8,628,798 B2* | 1/2014 | Halliday et al. ............ 424/468 |
| 2001/0014715 A1 | 8/2001 | Blum et al. |
| 2001/0044467 A1 | 11/2001 | Neal |

(56) References Cited

U.S. PATENT DOCUMENTS

| | | |
|---|---|---|
| 2001/0051656 A1 | 12/2001 | Place et al. |
| 2001/0051694 A1 | 12/2001 | Barges et al. |
| 2002/0004529 A1 | 1/2002 | Neal |
| 2002/0013304 A1 | 1/2002 | Wilson et al. |
| 2002/0028846 A1 | 3/2002 | Yeager et al. |
| 2002/0037491 A1 | 3/2002 | Halliday et al. |
| 2002/0039935 A1 | 4/2002 | Dewanjee |
| 2002/0045665 A1 | 4/2002 | Yeager et al. |
| 2002/0052407 A1 | 5/2002 | Lee et al. |
| 2002/0062097 A1 | 5/2002 | Simpson |
| 2002/0077442 A1 | 6/2002 | Gertzmann et al. |
| 2002/0077444 A1 | 6/2002 | Matsumoto et al. |
| 2002/0099003 A1 | 7/2002 | Wilson et al. |
| 2002/0115814 A1 | 8/2002 | Woodhouse et al. |
| 2002/0115976 A1 | 8/2002 | Fleming |
| 2002/0119833 A1 | 8/2002 | Dewanjee |
| 2002/0128314 A1 | 9/2002 | Neal |
| 2002/0132965 A1 | 9/2002 | Gertzmann et al. |
| 2002/0161009 A1 | 10/2002 | Leonardi et al. |
| 2003/0022022 A1 | 1/2003 | Kizumoto et al. |
| 2003/0032754 A1 | 2/2003 | Kaufhold et al. |
| 2003/0032759 A1 | 2/2003 | Fischer et al. |
| 2003/0045668 A1 | 3/2003 | Fischer et al. |
| 2003/0060589 A1 | 3/2003 | Shimizu et al. |
| 2003/0122282 A1 | 7/2003 | Plummer et al. |
| 2003/0129241 A1 | 7/2003 | Yeager et al. |
| 2003/0134903 A1 | 7/2003 | Yeager et al. |
| 2003/0144454 A1 | 7/2003 | Krebs et al. |
| 2003/0158369 A1 | 8/2003 | Slagel |
| 2003/0207852 A1 | 11/2003 | Place et al. |
| 2003/0212139 A1 | 11/2003 | Neal |
| 2004/0014761 A1 | 1/2004 | Place et al. |
| 2004/0044080 A1 | 3/2004 | Place et al. |
| 2004/0047910 A1 | 3/2004 | Beckett et al. |
| 2004/0110843 A1 | 6/2004 | Yeager et al. |
| 2004/0115229 A1 | 6/2004 | Roby |
| 2004/0131664 A1 | 7/2004 | Mo et al. |
| 2004/0142847 A1 | 7/2004 | Bayersdoerfer et al. |
| 2004/0157766 A1 | 8/2004 | Embil et al. |
| 2004/0265355 A1 | 12/2004 | Shalaby |
| 2004/0266688 A1 | 12/2004 | Nayak |
| 2005/0004226 A1 | 1/2005 | Lu et al. |
| 2005/0013793 A1 | 1/2005 | Beckman et al. |
| 2005/0031690 A1 | 2/2005 | Rohrs et al. |
| 2005/0048104 A1 | 3/2005 | Venkatraman et al. |
| 2005/0053639 A1 | 3/2005 | Shalaby |
| 2005/0053670 A1 | 3/2005 | Schaub |
| 2005/0070516 A1 | 3/2005 | Wilson et al. |
| 2005/0090474 A1 | 4/2005 | Naor |
| 2005/0095245 A1 | 5/2005 | Riley et al. |
| 2005/0161030 A1 | 7/2005 | Robert et al. |
| 2005/0169975 A1 | 8/2005 | Suzuki et al. |
| 2005/0181030 A1 | 8/2005 | Mo et al. |
| 2005/0187342 A1 | 8/2005 | Schieferstein et al. |
| 2005/0208152 A1 | 9/2005 | Milankovits |
| 2005/0238722 A1 | 10/2005 | Pathak et al. |
| 2005/0245902 A1 | 11/2005 | Cornish et al. |
| 2006/0003950 A1 | 1/2006 | Strugnell et al. |
| 2006/0018951 A1 | 1/2006 | Maniar et al. |
| 2006/0041021 A1 | 2/2006 | Wilson et al. |
| 2006/0052341 A1 | 3/2006 | Cornish et al. |
| 2006/0078616 A1 | 4/2006 | Georgewill et al. |
| 2006/0093675 A1 | 5/2006 | Ebmeier et al. |
| 2006/0134161 A1 | 6/2006 | Halliday |
| 2006/0183724 A1 | 8/2006 | Diliberti et al. |
| 2006/0210599 A1 | 9/2006 | Gibson et al. |
| 2007/0043332 A1 | 2/2007 | Malcolm et al. |
| 2007/0128154 A1 | 6/2007 | Hadba et al. |
| 2007/0135605 A1 | 6/2007 | Hadba et al. |
| 2007/0148105 A1 | 6/2007 | Spector |
| 2007/0155906 A1 | 7/2007 | Hissink et al. |
| 2007/0166382 A1 | 7/2007 | Kiser et al. |
| 2007/0282093 A1 | 12/2007 | Yoshimura et al. |
| 2008/0009663 A1 | 1/2008 | Bartning et al. |
| 2008/0009666 A1 | 1/2008 | Bartning et al. |
| 2008/0108775 A1 | 5/2008 | Schieferstein et al. |
| 2008/0140185 A1 | 6/2008 | Kiser et al. |
| 2008/0145419 A1 | 6/2008 | Gibson et al. |
| 2008/0152708 A1 | 6/2008 | Gibson et al. |
| 2008/0199511 A1 | 8/2008 | Sitruk-Ware et al. |
| 2008/0206310 A1 | 8/2008 | Davis |
| 2008/0207571 A1 | 8/2008 | Davis |
| 2008/0262613 A1 | 10/2008 | Gogolewski |
| 2008/0271190 A1 | 10/2008 | Holland |
| 2008/0286339 A1 | 11/2008 | Ron et al. |
| 2009/0004246 A1 | 1/2009 | Woolfson et al. |
| 2009/0011209 A1 | 1/2009 | Steinberger et al. |
| 2009/0060982 A1 | 3/2009 | Ron et al. |
| 2009/0061172 A1 | 3/2009 | Hayashi et al. |
| 2009/0081278 A1 | 3/2009 | De Graaff et al. |
| 2009/0203591 A1 | 8/2009 | Bagchi et al. |
| 2009/0203772 A1 | 8/2009 | Villanueva et al. |
| 2009/0291120 A1 | 11/2009 | Tuominen et al. |
| 2010/0104619 A1 | 4/2010 | De Graaff et al. |
| 2010/0203104 A1 | 8/2010 | De Graaff et al. |
| 2010/0285094 A1 | 11/2010 | Gupta |
| 2011/0045076 A1 | 2/2011 | Kiser et al. |
| 2011/0056501 A1 | 3/2011 | Kortesuo et al. |
| 2011/0059040 A1 | 3/2011 | Kiser et al. |
| 2011/0077578 A1 | 3/2011 | Bartning et al. |
| 2011/0091488 A1 | 4/2011 | Halliday et al. |
| 2011/0150955 A1 | 6/2011 | Klingman |

FOREIGN PATENT DOCUMENTS

| | | |
|---|---|---|
| EP | 335669 | 3/1989 |
| EP | 424164 | 10/1990 |
| EP | 0450176 | 10/1991 |
| EP | 0401990 | 1/1992 |
| EP | 1063942 | 6/2004 |
| FR | 2557576 | 7/1985 |
| FR | 2705567 | 12/1994 |
| GB | 2047093 | 11/1980 |
| GB | 2047094 | 11/1980 |
| GB | 2244920 | 12/1991 |
| JP | 5600253 | 3/1980 |
| JP | 1135488 | 2/1983 |
| JP | 0670952 | 3/1994 |
| JP | 1150610 | 6/1999 |
| JP | 200502691 | 3/2000 |
| JP | 2001513550 | 9/2001 |
| JP | 2002515069 | 5/2002 |
| WO | 1980001984 | 10/1980 |
| WO | 8905319 | 6/1989 |
| WO | 8907117 | 8/1989 |
| WO | 9102763 | 3/1991 |
| WO | 9403510 | 2/1994 |
| WO | 9413724 | 6/1994 |
| WO | 9422934 | 10/1994 |
| WO | 9606875 | 3/1996 |
| WO | 9615171 | 5/1996 |
| WO | 96038153 | 5/1996 |
| WO | 9621427 | 7/1996 |
| WO | 9631551 | 10/1996 |
| WO | 9717386 | 5/1997 |
| WO | 9724109 | 7/1997 |
| WO | 1997024109 | 7/1997 |
| WO | 1998056323 | 12/1998 |
| WO | 1999009964 | 3/1999 |
| WO | 9947073 | 9/1999 |
| WO | 9947127 | 9/1999 |
| WO | 9956731 | 11/1999 |
| WO | 0000222 | 1/2000 |
| WO | 0040222 | 7/2000 |
| WO | 0203896 | 1/2002 |
| WO | 0209631 | 2/2002 |
| WO | 03087183 | 10/2003 |
| WO | 05116100 | 2/2005 |
| WO | 05063145 | 7/2005 |
| WO | 05089778 | 9/2005 |
| WO | 06048639 | 5/2006 |
| WO | 09094573 | 7/2009 |
| WO | 1035837 | 4/2010 |

(56) References Cited

FOREIGN PATENT DOCUMENTS

| WO | 10119029 | 5/2010 |
|----|----------|--------|
| WO | 11011099 | 1/2011 |
| WO | 11039418 | 4/2011 |

OTHER PUBLICATIONS

Baimak et al., "Synthesis and characterization of poly(I-lactide-co-e-caprolactone) copolymers: Effect of stannous octoate initiator and diethylel glycol coinitiator concentration." ScienceAsia 30 (2004):324-334.
Casteneda, C.S., et al. "Misoprostol Dose Selection in a Controlled-Release Vaginal Insert for Induction of Labor in Nulliparous Women," American Journal of Obstetrics and Gynecology, 193:1071-1075, (Sep. 2005).
Chen, "Stabilization and sustained-release effect of Misoprostol with Methacrylate copolymer", International Journal of Pharmaceutics, 203 (2000) pp. 141-148.
Jianzhong et al. "Polycaprolactone-poly(ethylene glycol) block copolymer III Drug release behavior." Chinese J Polym Sci., 13(2) 1995:154:161.
Kararli, "Stabilization of Misoprostol with Hydroxypropyl Methylcellulose (HMPC) Against Degradation by Water", Pharmaceutical Research, vol. 7, No. 11 (1990).
Lee JW, et al., "Thermoreversible gelation of biodegradable poly(epsilon-caprolactone) and poly(ethylene glycol)multiblock copolymers in aqueous solutions." J Control Release. Jun. 15, 2001; 73(2-3):315-27.
Leiva et al., "Poly(£-caprolactone)-block-poly(ethyleneoxide) -block-poly(£-V caprolactone): Biodegradable triblock copolymer spread at the air-water interface." European Polymer Journal 44(8), Aug. 2008:2589-2598.
Merck Index (Ninth Edition, 1976, p. 4073).
PCT/GB2003/004208 International Search Report dated Jan. 2, 2004.
PCT/GB2005/002951 Written Opinion of the International Searching Authority dated Oct. 6, 2005.
PCT/GB2005/002951 International Preliminary Report on Patentability dated Feb. 6, 2007.
PCT/GB2007/002604, International Search Report, dated Jul. 12, 2007.
PCT/GB2007/002604 Written Opinion of International Searching Authority dated Jul. 12, 2007.
PCT/GB2005/002951 International Search Report dated Oct. 20, 2005.
PCT/GB2007/002401 International Search Report dated Oct. 24, 2007.
PCT/GB2007/002401 Written Opinion of the International Searching Authority dated Oct. 24, 2007.
PCT/GB2007/002415 International Search Report dated Oct. 30, 2007.
PCT/GB2007/002415 Written Opinion of the International Searching Authority dated Oct. 30, 2007.
Santerre, et al., "Understanding the biodegradation of polyurethanes: From classical implants to tissue engineering materials." Biomaterials 26(35), Dec. 2005: 7457-7470.
Sato et al., The effects of a prostaglandin El analogue, misoprostol, on gastric mucosal blood volume index and haemoglobin oxygenation in humans, Journal of Gastroenterology and Hepatology, 2008, 2(6), 499-505.
Tyagi, P., et al., "Sustained Intravesical Drug Delivery Using Thermosensitive Hydrogel," Pharmaceutical Research, 21 (5):832-837 (May 2004).
Yu, J., et al. "Blood interactions with novel polyurethaneurea hydrogels," Biomaterials 12(2): 119-120 (1991).
Zhou et al., "Biodegradable poly(e-caprolactone)-poly(ethylene glycol) block copolymers: characterization and their use as drug carriers for a controlled delivery system." Biomaterials (2003) 24(20):3563-3570.
U.S. Appl. No. 11/777,175, filed Jul. 12, 2007.
U.S. Appl. No. 12/835,436, filed Jul. 13, 2010.
U.S. Appl. No. 13/571,596, filed Oct. 8, 2012.
U.S. Appl. No. 11/573,256, filed Feb. 5, 2007.
U.S. Appl. No. 13/429,678, filed Mar. 26, 2012.
U.S. Appl. No. 13/906,905, filed May 31, 2013.
U.S. Appl. No. 12/307,514, filed Jan. 5, 2009.
U.S. Appl. No. 12/373,002, filed Jan. 8, 2009.
U.S. Appl. No. 13/605,689, filed Sep. 6, 2012.
U.S. Appl. No. 12/446,235, filed Apr. 18, 2009.

* cited by examiner

WATER-SWELLABLE POLYMERS

CROSS-REFERENCE TO RELATED APPLICATIONS

This application is a continuation of U.S. application Ser. No. 13/571,596, filed Aug. 10, 2012, which is a continuation of U.S. application Ser. No. 12/835,436, filed Jul. 13, 2010, which is a divisional of U.S. application Ser. No. 10/528,875, filed Mar. 23, 2005, which is a National Stage filing under 35 U.S.C. 371 of International Application PCT/GB2003/004208, filed Sep. 26, 2003, which claims priority from United Kingdom Patent Application No. 0222522.5, filed Sep. 27, 2002. The specifications of the parent applications are incorporated by reference herein. International Application PCT/GB2003/004208 was published under PCT Article 21(2) in English.

TECHNICAL FIELD

The present invention relates to water-swellable linear polymers, suitable for the production of controlled release compositions for release of pharmaceutically active agents over a prolonged period of time.

BACKGROUND

Certain cross-linked polyurethane polymers are known from European Patent Publication EP0016652 and EP0016654. These patent specifications describe cross-linked polyurethanes formed by reacting a polyethylene oxide of equivalent weight greater than 1500 with a polyfunctional isocyanate and a trifunctional compound reactive therewith, such as an alkane triol. The resultant cross-linked polyurethane polymers are water-swellable to form a hydrogel but are water-insoluble and may be loaded with water-soluble pharmaceutically active agents. One particular polyurethane polymer is the reaction product of polyethylene glycol 8000, Desmodur (DMDI i.e. dicyclohexylmethane-4,4-diisocyanate) and 1,2,6-hexane triol and which has been used commercially for vaginal delivery of prostaglandins.

However, such polyurethane polymers possess a number of practical disadvantages. Whilst the use of a triol cross-linking agent is effective in providing polymers of relatively reproducible swelling characteristics, the percent swelling is typically 200-300% (i.e. the increase in weight of the swollen polymer divided by the weight of the dry polymer). Pharmaceutically active agents are loaded by contacting the dry polymer with an aqueous solution of pharmaceutically active agent, such that the solution becomes absorbed into the polymer, forming a hydrogel. The swollen polymer is then dried back to a chosen water content before use. A consequence is that with the conventional cross-linked polyurethane, the degree of swelling limits the molecular weight of the pharmaceutically active agent which can be absorbed into the hydrogel structure to below about 3000. A further disadvantage is that only water-soluble pharmaceutically active agents may be used. Finally, since the conventional cross-linked polyurethane polymer is essentially insoluble in both water and organic solvents, processing of the formed polymer into other solid forms, such as films or coatings, is not possible.

The object of the present invention is to provide a polyurethane polymer of the aforementioned type which is not cross-linked but is linear but which still possesses the desirable properties of reproducible swellability found in the prior cross-linked polyurethanes.

Initial work on the production of linear polyurethane polymers proved unsatisfactory, since the polymers were not stable but continued to react over extended time periods. Also, the swellability was not constant or reproducible, and changed with time.

DETAILED DESCRIPTION

Figure 1:
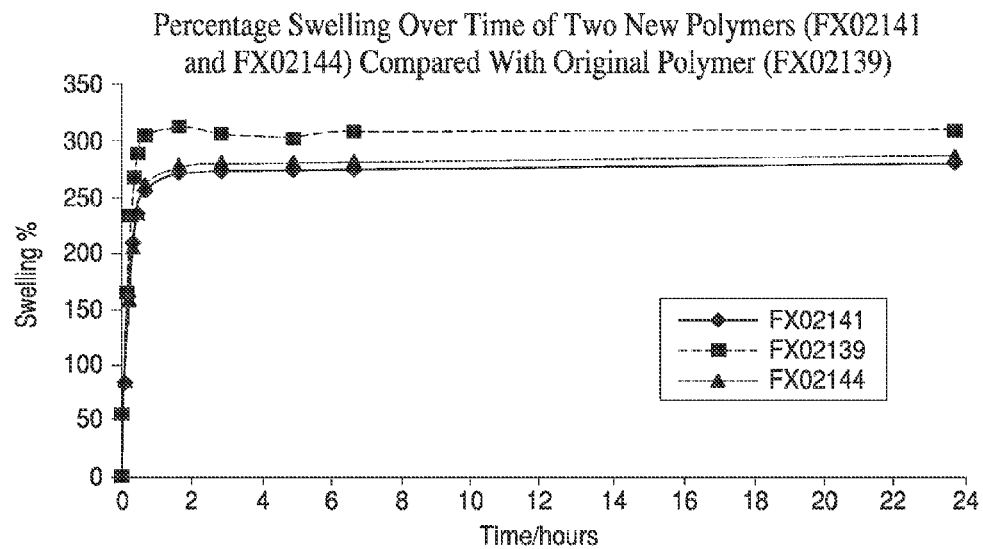
FIG. 1 graphically shows percentage swelling over time of two new polymers compared with original polymer.

The present invention is based on the discovery that linear polyurethanes having suitable characteristics may be obtained by reacting a polyoxyethylene glycol with a diol or other difunctional compound and a difunctional isocyanate.

In particular, the present invention provides a water-swellable linear polymer obtainable by reacting together
(a) a polyethylene oxide;
(b) a difunctional compound; and
(c) a difunctional isocyanate.

Alternatively stated, the invention provides a water-swellable linear polyurethane formed of moieties derived from (a), (b) and (c) bonded together.

The linear polymer produced is swellable in water to an enhanced degree, depending upon the ratio of the three components (a), (b) and (c), for example up to 500%, up to 800% or even above 1,000%, thus allowing higher molecular weight pharmaceutically active water-soluble agents to be loaded into the swollen hydrogel derived from the linear polymer. Usually, the polymer is swellable to 200% to 2000%, for example 250 to 1700%. Depending on the particular active agent, swellabilities in the ranges 300-1000, 400-800, 1000-1500, 1100-1300 etc., may be achieved with the polyurethanes of the invention. The linear polymer of the invention is also soluble in certain organic solvents, such as dichloromethane, which allows the polymer to be dissolved and cast into films or coatings. It also allows active agents of poor water solubility but which are soluble in organic solvents, to be loaded into the polymer.

In this description the term "equivalent weight" is used as meaning the number average molecular weight divided by the functionality of the compound.

Polyethylene oxides contain the repeat unit $(CH_2CH_2O)$ and are conveniently prepared by the stepwise addition of ethylene oxide to a compound containing a reactive hydrogen atom. Polyethylene glycols are prepared by the addition of ethylene oxide to ethylene glycol to produce a difunctional polyethylene glycol structure $HO(CH_2CH_2O)_nH$ wherein n is an integer of varying size depending on the molecular weight of polyethylene oxide. Polyethylene oxides used in the present invention are generally linear polyethylene glycols i.e. diols having an equivalent weight of 1500 to 20,000, particularly 3000 to 10,000 and especially 4000 to 8000. Molecular weights are usually in the region 4000 to 35,000.

The difunctional compound is reactive with the difunctional isocyanate, and is typically a difunctional amine or diol. Diols in the range $C_5$ to $C_{20}$, preferably $C_8$ to $C_{15}$ are preferred. Thus, decane diol has been found to produce particularly good results. The diol may be a saturated or unsaturated diol. Branched diols may be used but straight chain diols are preferred. The two hydroxy groups are generally on terminal carbon atoms. Thus, preferred diols include 1,6-hexanediol, 1,10-decanediol, 1,12-dodecanediol and 1,16-hexadecanediol.

The difunctional isocyanate is generally one of the conventional diisocyanates, such as dicyclohexylmethane-4,4-diisocyanate, diphenylmethane-4,4-diisocyanate, 1,6-hexamethylene diisocyanate etc.

The ratio of the components (a) to (b) to (c) (in terms of equivalent weights) is generally in the range 0.1-1.5 to 1 to 1.1-2.5, particularly 0.2-0.9 to 1 to 1.2-1.9. A preferred range is 0.5-0.9 to 1 to 1.5-1.9. Of course, the skilled man through reasonable experimentation would determine the best ratio of ingredients to give the desired properties. The amount of component (c) is generally equal to the combined amounts of (a) and (b) to provide the correct stoichiometry.

Polymers produced at extreme ends of the ranges may not necessarily give optimal properties. For example, high amounts of (a) polyethylene oxide may undesirably lead to the polymer being water-soluble. Small amounts may reduce the percentage swelling. Generally, the ratio of (a) polyethylene oxide to (b) difunctional compound is preferably 0.1-1.5 to one, preferably 0.2-0.9 to one.

The polymers are generally produced by melting the previously dried polyethylene glycol together with the difunctional compound (e.g. diol) at a temperature of around 85° C. A catalyst such as ferric chloride is incorporated. The molten mixture is dried under vacuum to remove excess moisture and the diisocyanate added thereto. The reaction mixture is then poured into billet moulds and cured for a specified time. Thus, the polymer is initially formed as a moulded solid. However, the linear polymers of the present invention are soluble in certain organic solvents. This allows the polymer to be dissolved and the resultant solution cast to form films. The solution may also be employed for coating granules, tablets etc., in order to modify their release properties. Alternatively, the solution can be poured into a non-solvent so as to precipitate polymer/active microparticles.

Thus, the invention also provides controlled release compositions comprising the linear polymer together with an active agent. The active agent may be a pharmaceutically active agent for human or animal use. It may also be any other agent where sustained release properties (e.g. algicides, fertilisers etc.) are required. The pharmaceutical solid dosage forms include suppositories, pessaries for vaginal use, buccal inserts for oral administration etc. These dosage forms are generally administered to the patient, retained in place until delivery of active agent has occurred and the spent polymer is then removed.

The linear polymer of the present invention may be swollen to a higher degree than the conventional cross-linked polymer and is thus suitable for the uptake of high molecular weight pharmaceutically active agents (up to and exceeding a molecular weight of 3000 e.g. up to 10,000, up to 50,000, up to 100,000 or even up to 200,000 depending on swellability) and is thus particularly suitable for the uptake and delivery of proteins and peptides. Generally, the molecular weight of the active agent is in the range 200 to 20,00. A wide variety of water-soluble pharmaceutically active substances such as those listed in EP0016652 may thus be incorporated. Furthermore, the linear polymers of the present invention may be loaded with pharmaceutically active agents which are poorly water-soluble, provided that these can be dissolved in a common solvent with the polymer. The resultant solution can then be cast into any desired solid forms. Pharmaceutically active agents of particular interest include:

Proteins e.g. interferon alpha, beta and gamma, insulin, human growth hormone, leuprolide; Benzodiazepines e.g. midazolam; Anti-migraine agents e.g. triptophans, ergotamine and its derivatives; Anti-infective agents e.g. azoles, bacterial vaginosis, candida; and opthalmic agents e.g. latanoprost.

A detailed list of active agent includes $H_2$ receptor antagonist, antimuscaririe, prostaglandin analogue, proton pump inhibitor, aminosalycilate, corticosteroid, chelating agent, cardiac glycoside, phosphodiesterase inhibitor, thiazide, diuretic, carbonic anhydrase inhibitor, antihypertensive, anti-cancer, antidepressant, calcium channel blocker, analgesic, opioid antagonist, antiplatel, anticoagulant, fibrinolytic, statin, adrenoceptor agonist, beta blocker, antihistamine, respiratory stimulant, micolytic, expectorant, benzodiazepine, barbiturate, anxiolytic, antipsychotic, tricyclic antidepressant, $5HT_1$ antagonist, opiate, 5HT, agonist, antiemetic, antiepileptic, dopaminergic, antibiotic, antifungal, anthelmintic, antiviral, antiprotozoal, antidiabetic, insulin, thyrotoxin, female sex hormone, male sex hormone, antioestrogen, hypothalamic, pituitary hormone, posterior pituitary hormone antagonist, antidiuretic hormone antagonist, bisphosphonate, dopamine receptor stimulant, androgen, non-steroidal anti-inflammatory, immuno suppressant local anaesthetic, sedative, antipsioriatic, silver salt, topical antibacterial, vaccine.

The invention also provides a method of manufacturing the linear polymer by reacting together components (a), (b) and (c).

Embodiments of the present invention will now be described by way of example only in Sections A and B.

Tests Carried Out on New Linear Polymer

All batches of linear polymer according to the invention were tested as follows.

I. Appearance.

The polymer should be free of air bubbles.

II. Percentage Swelling.

Accurately weigh each of ten slices (to 3 decimal places) and note the dry weight (mark each slice with an ID number). Swell the slices in 300 ml demineralised water at 25° C.±1° C. in a water bath for 24 hours. Remove slices and blot dry with a paper towel. Reweigh each slice and determine the swelling factor as follows:

$$\% \text{ Swelling (pph)} = \frac{\text{Swollen weight} - \text{dry weight} \times 100}{\text{dry weight}} \quad 1$$

III. Percent Water Soluble Extractables (% WSE).

Wash thoroughly and dry loss-on-drying vessels in an oven, overnight at 105° C., cool for 2 hours in a desiccator and then weight. Record weight to 4 decimal places.

Accurately weigh out 10 slices and put into a 250 ml conical flask. Add 150 ml demineralised water and swirl gently for 30 seconds. Decant the water and repeat. To the rinsed pessaries add 50 ml demineralised water. Shake on a flat bottom shaker for 24 hours at room temperature.

Prepare 2 blanks (water only) and 2 samples (water+ extract) each time the determination is carried out. Calculate each individual blank determination and the mean of these two values. This is to be used to obtain the Corrected Total Weight.

Decant the water from the slices and pass ca 10 ml of the water (using a plastic syringe) through a Millipore filter (1.2 um) into a previously weighted LOD vessel and weigh again. Place in an oven at 105° C. and evaporate sample to dryness (18 hours/overnight). Remove from oven, cool for 2 hours in a dessicator and weigh.

Calculation—(All Weights in Grams)

$$\text{Total Wt of Blank} = \text{Wt of Residue In } LOD \text{ Vessel} \times \frac{50}{\text{Wt of water added To } LOD \text{ Vessel}}$$

$$\text{Total Wt of Extract} = \text{Wt of Extract In } LOD \text{ Vessel} \times \frac{50}{\text{Wt of sample added To } LOD \text{ Vessel}}$$

$$\text{Corrected Total } Wt = Wt \text{ of Extract} - Wt \text{ of blank}$$

$$\% \text{ (w/w) Water Soluble Extractables} = \frac{\text{Corrected Wt of Extract}}{\text{Wt of Pessaries Used}} \times 100$$

IV. Crystallinity.

Cut a small portion from the slice and seal in a 50 ul aluminium pan. Prepare a sealed empty pan of the same dimensions as a reference. Place the pans in the sample and reference holders respectively and run the temperature programme. Calculate the onset temperature and enthalpy using the Data Station. Crystallinity is equal to the ratio of the melt enthalpy of sample to melt enthalpy of 100% crystalline polyethylene oxide, enthalpies expressed in joules/g.

$$\% \text{ crystallinity} = \frac{\text{Enthalpy of sample}}{220.12} \times 100$$

V. Percentage Swelling 72 Hours
VI. Percentage Swelling 144 hours

These percentage-swelling tests were carried out as the standard percentage-swelling test but the total incubation time was increased from 24 hours to either 72 or 144 hours.

Further selective tests included:

VII. Percentage Swelling Over Time

Where three slices of each polymer batch tested were immersed in water and weighed at time intervals over a 24-hour period[10]. The percentage swelling was then calculated from these weights.

VIII. Stability Testing

Samples were tested for stability at 40° C. over a four-week period. At the specified time point intervals of one, two and four weeks the percentage swelling (24 hours) was calculated and used as an indication of polymer stability.

IX. Solubility in Different Solvents

Three polymer slices of each batch tested were placed into separate vials for each solvent used. For each batch, the different slices were tested twice using either whole or cut slices and to each vial around 10 mL of solvent was added. The solvents used were acetone, dichloromethane, ethanol and methanol.

X. Water Solubility Testing

Ten slices of each batch tested were placed in a conical flask and around 300 mL of demineralised water was added. The flasks were placed on a flat bottom shaker for seven days.

Section A

A1. Polymer Manufacture

Various stoichiometric ingredient ratios of PEG:DD: DMDI were used to produce new polymers. Altering the ingredient ratio resulted in a change in the properties of the polymer. PEG is polyethylene glycol; DD is decane-1,10-diol; and DMDI is dicyclohexylmethane-4,4-diisocyanate.

TABLE 1

New Polymers Manufactured

| PEG:DD:DMDI | Batch Numbers |
|---|---|
| 1:1:2 | FX02140, FX02143 |
| 0.7:1:1.7 | FX02158 |
| 0.5:1:1.5 | FX02148 |
| 0.25:1:1.25 | FX02141, FX02144, FX02149, FX02161 |

(The ratio of the known cross-linked polymer FX02139 used for comparison is PEG8000:hexanetriol:DMDI of 0.8: 1.0:2.3)

PEG and DD were weighed into a round-bottomed flask balance and melted overnight at a temperature of 85° C.

The required amount of ferric chloride ($FeCl_3$) plus an excess was weighed into a tared 200 mL beaker with spatula. This was made up to 100 g with molten PEG/DD from the previous step. This mixture of PEG/DD/$FeCl_3$ was stirred vigorously and kept in the oven at 85° C., with frequent stirring, until required.

The remaining molten PEG/DD was dried under vacuum at 95° C. for one and a half hours to remove excess moisture. The moisture content of the PEG/DD was tested using the volumetric Karl Fischer titration method with the specification for moisture being set at no more than 0.05%.

Next, 80 g of the PEG/DD/$FeCl_3$ mixture was weighed into a 2 L jug and this ensured the correct weight of $FeCl_3$. The amount of PEG/DD required, taking into account the 80 g already present from the PEG/DD/$FeCl_3$ mixture, was then added to the 2 L jug which was returned to the oven whilst setting up the equipment in the fume cupboard.

A mixer set at 427 rpm was used to agitate the contents of the 2 L jug for 150 seconds, and the DMDI was added during the first 30 seconds.

This final mixture was then poured from the 2 L jug into billet moulds, placed in an oven at 95° C. and cured for a specified time, which ranged from 10 to 30 hours. After this time, the oven was turned off and the billets left to cool to ambient.

The polymer was then demoulded, and the resultant polymer slabs sliced.

A2. Polymer Properties (a) Characteristics of New Polymer

The characteristics of the new polymer batches manufactured are summarised in Tables 2-5.

TABLE 2

New polymer with a PEG:DD:DMDI ratio of 1:1:2

|  | FX00206 (FK) | FX01153 (VJ) | FX01167 (VJ) | FX02140 (SS) | FX02143 (SS) |
|---|---|---|---|---|---|
| Cure Time | 20 hours 10 minutes | 20 hours | 20 hours | 10 hours | 20 hours |
| Appearance | Normal looking |  |  | Normal looking but darker in colour than original polymer | Normal looking but darker in colour than original polymer |
| Percentage Swelling | 646%* | 1334.14% RSD 1.82 | 1918% RSD 2.58 | 1110% RSD 0.8 | 1320% RSD 4.37 |
| % WSE | 0.35% | 2.03%** | 7.54%** | 1.11%** | 1.24%** |

*Polymer not sliced but cut into relatively thick slices
**Filtrate too thick for filter paper It was found that the new polymer with a PEG:DD:DMDI ratio of 1:1:2 lost its integrity during the water soluble extractable testing and one further test of water solubility was carried out on this ingredient ratio to confirm this. These polymers were apparently water soluble to an extent and therefore unsuitable.

TABLE 3

New polymer with a PEG:DD:DMDI ratio of 0.25:1:1.25

|  | FX01156 (VJ) | FX02141 (SS) | FX02144 (SS) | FX02149 (SS) | FX02161 (SS) |
|---|---|---|---|---|---|
| Cure Time | 20 hours | 10 hours | 10 hours | 20 hours | 30 hours |
| Appearance | Golden yellow; undissolved FeCl present; waxy | Golden yellow; undissolved FeCl present; waxy | Normal looking but darker in colour than original polymer | Darker colour than original polymer; undissolved FeCl present | Darker colour than original polymer; some undissolved FeCl |
| Percentage Swelling | 427.41% RSD 0.58 | 284% RSD 1.09 | 287% RSD 0.77 | 304% RSD 0.62 | 304% RSD 0.35 |
| % WSE | 1.23% | 0.16% | 0.44% | 0.24% | 0.02% |
| Crystallinity |  | 43.63% RSD 2.24 | 43.33% RSD 1.46 | 44.50% RSD 0.50 | 44.02% RSD 0.96 |

TABLE 4

New polymer with a PEG:DD:DMDI ratio of 0.5:1:1.5

|  | FX01197 (VJ) | FX02070 (LC) | FX02148 (SS) |
|---|---|---|---|
| Cure Time | 20 hours | 20 hours | 10 hours |
| Appearance |  |  | Darker colour than original polymer; air bubbles present; some undissolved FeCl present |
| Percentage Swelling | 422.4% RSD 0.69 | 347% RSD 2.6 | 492% RSD 1.35 |
| % WSE |  | 0.1214% | 0.1% |
| Crystallinity |  |  | 49.69% RSD 0.47 |

TABLE 5

New polymer with a PEG:DD:DMDI ratio of 0.7:1:1.7

|  | FX02158 (SS) |
|---|---|
| Cure Time | 10 hours |
| Appearance | Darker in colour than original polymer |
| Percentage Swelling | 730% RSD 0.94 |
| % WSE | 0.73% |
| Crystallinity | 49.6% RSD 2.06 |

(b) Extended Percentage Swelling

TABLE 6

Results of Swelling at 24, 72 and 114 Hours

| Batch Number | Percentage Swelling 24 Hours | Percentage Swelling 72 Hours | Percentage Swelling 144 Hours | Percentage Increase from 24 to 144 Hours |
|---|---|---|---|---|
| FX02141 | 284% RSD 1.09 | 291% RSD 0.51 | 293% RSD 0.77 | 3% |
| FX02144 | 287% RSD 0.77 | 299% RSD 0.33 | 300% RSD 0.51 | 5% |
| FX02149 | 304% RSD 0.62 | 311% RSD 0.99 | 318% RSD 1.00 | 5% |
| FX02161 | 304% RSD 0.35 | 308% RSD 0..43 | 313% RSD 0.66 | 3% |
| FX02148 | 492% RSD 1.35 | 504% RSD 1.04 | 529% RSD 2.20 | 8% |
| FX02158 | 730% RSD 206 | 786% RSD 3.36 | 827% RSD 3.36 | 13% |
| FX02139 (cross-linked) | 308% RSD 0.59 |  | 298% RSD 0.76 | −3% |

Figure 2:
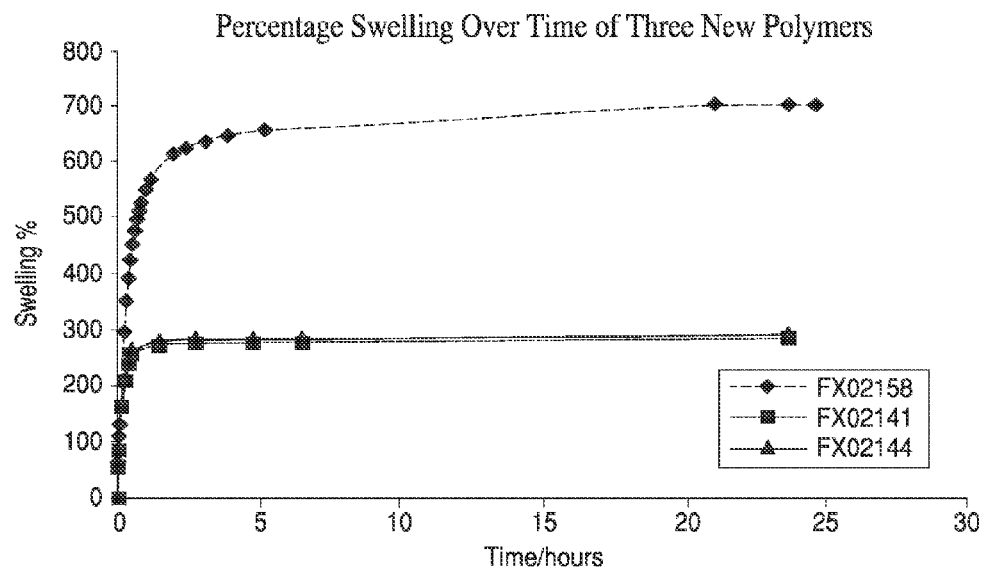
FIG. 2 graphically shows percentage swelling over time of three new polymers.

(c) Percentage Swelling Over Time is given in FIGS. 1 and 2:

FIG. 1 shows Percentage Swelling Over Time of Two New Polymers (FX02141 and FX02144) Compared With Original Polymer (FX02139); and FIG. 2 shows Percentage Swelling Over Time of Three New Polymers (d) Stability of Linear Polymer

TABLE 7

Stability Testing of FX02150 (Purified FX02144)

| Time | Percentage Swelling |
|---|---|
| 0 (FX02144) | 287% RSD 0.77 |
| 1 week | 370% RSD 4.57 |
| 2 week | 374% RSD 5.10 |
| 4 week | 379% RSD 2.81 |

(g) Solubility Testing of Linear Polymer

TABLE 8

Solubility Testing of New Polymer in Four Different Solvents

| Batch Number | Acetone | Dichloromethane | Ethanol | Methanol |
|---|---|---|---|---|
| FX02244 | Polymer not swollen; slices white and in small pieces; forms suspension on shaking but rapidly sediments | Polymer dissolved resulting in a clear solution | Polymer swollen, slices opaque and intact; slices appear smooth | Polymer swollen & broken up, opaque & still visible - settles to bottom |
| FX02148 | Polymer not swollen; slices white & breaking up | Polymer dissolved resulting in a clear solution | Polymer swollen, slices opaque and intact; slices appear smooth | Polymer dissolved resulting in a clear solution |
| FX02158 | Polymer not swollen; slices white; break up on vigorous shaking | Polymer dissolved resulting in a clear solution | Polymer swollen; slices slightly opaque; appear textured | Polymer dissolved resulting in a clear solution |
| FX02140 | Polymer not swollen; slices white; break up on vigorous shaking | Polymer dissolved resulting in a clear solution | Polymer swollen; slices clear and textured looking | Polymer dissolved resulting in a clear solution |

TABLE 9

Solubility Testing of New Polymer in Water

| Batch Number | Results |
|---|---|
| FX02244 | Slices swollen and opaque. No signs of dissolving. Water clear |
| FX02148 | Slices swollen and opaque. No signs of dissolving. Water clear |
| FX02158 | Slices swollen and opaque. No signs of dissolving. Water clear |
| FX02140 | Slices lose their integrity and ultimately dissolve. Water frothy |

A3. Controlled Release Compositions

Dissolution Testing

A dosage form when placed into a vessel containing liquid media will release drug in a defined manner dictated by the formulation. This process known as dissolution can be used as an in vitro marker of the mechanism of release in the body. Sampling is carried out at regular intervals over a period of several hours and the amount of drug in the samples is analysed by spectrophotometer or HPLC. The data are normally represented as the release of labelled content against time.

(i) Pilocarpine

Potency

Ten units are swollen, macerated and quantitatively extracted into 500 ml of mobile phase. Pilocarpine is then assayed by HPLC relative to a reference standard. Detection is by UV spectrophotometer. The method is capable of detecting pilocarpine and its main degradation products, pilocarpic acid, iso-pilocarpine and iso-pilocarpic acid. The method is based upon the European Pharmacopeia method for pilocarpine.

Dissolution

Pilocarpine in vitro release from the units is performed by a USP paddle method at 50 rpm, 37° C. The pilocarpine released is assayed by HPLC as in the potency method.

Purification and Loading

The blank polymer slices are placed in purified water and agitated at about 4° C. for approximately 16-20 hours; the water is then decanted. Water swollen polymer slices are placed in an ethanol:water solution and agitated at about 4° C. for approximately 6-8 hours. The slices are then dried. Pilocarpine is dissolved in water which is then added to the dry polymer slices. The slices and drug loading solution are agitated at approximately 4° C. for approximately 16-20 hours to allow the uptake of drug. At the end of the dosing period the remaining drug solution is decanted and the swollen polymer slices are dried for 18-28 hours.

Polymer batch FX02144 was purified (FX02150) and then loaded with pilocarpine (FX02151).

Figure 3:
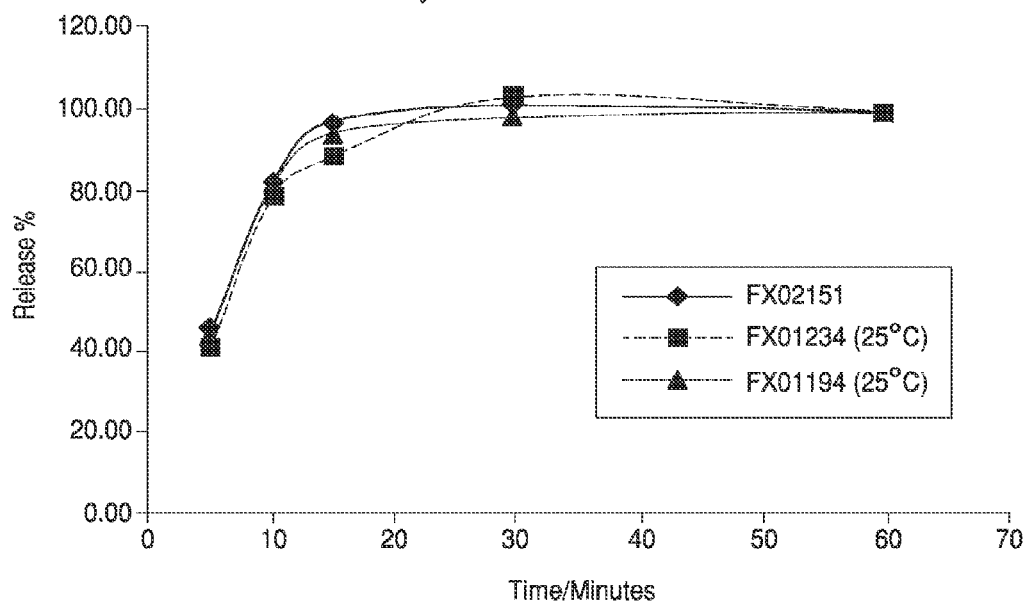
FIG. 3 graphically shows normalized graph of percentage pilocarpine released against time for linear polymer compared with original polymer.

FIG. 3 shows normalised graph of percentage Pilocarpine released against time for linear polymer FX02151 compared with original cross-linked polymers FX01234 and FX01194.

(ii) Loading with PGE$_2$ (Dinoprostone)

Potency

Ten units are swollen, macerated and quantitatively extracted into 500 ml of mobile phase. Dinoprostone is then assayed by HPLC relative to a reference standard. Detection is by UV spectrophotometer. The method is capable of detecting Dinoprostone and its main degradation products, PGA2, 8-iso PGE2 and 15 keto-PGE2. The method is based upon the EP method for dinoprostone.

Dissolution

Dinoprostone in vitro released from the units is performed by a USP paddle method at 50 rpm, 37° C. The dinoprostone released is assayed by HPLC as in the potency method.

Purification and Loading

The blank polymer slices are placed in purified water and agitated at about 4° C. for approximately 6-8 hours, then the water is decanted. The swollen slices are again placed in purified water and agitated at about 4° C. for approximately 16-20 hours; the water is then decanted. Water swollen polymer slices are placed in an ethanol:water solution and agitated at about 4° C. for approximately 6-8 hours. A solution of Dinoprostone is made by dissolving the appropriate amount of Dinoprostone in ethanol. The resulting solution is added to water and ethanol. This makes up the drug loading solution which is then added to the swollen polymer slices to give a 25% w/w ethanol:water mix. The slices and drug loading solution are agitated at approximately 4° C. for approximately 16-20 hours to allow the uptake of drug. At the end of the dosing period the remaining drug solution is decanted and the swollen polymer slices are dried for 18-28 hours.

Prostaglandin $E_2$ was loaded by an analogous process into a batch of cross-linked polymer (FX02139, loaded FX02159) and a batch of linear polymer (FX02144, loaded FX02157), both with 0.6 mm thick slices. The measured potencies were 9.4 mg (FX02159, control) and 9.7 mg (FX02157) respectively.

Figure 4:
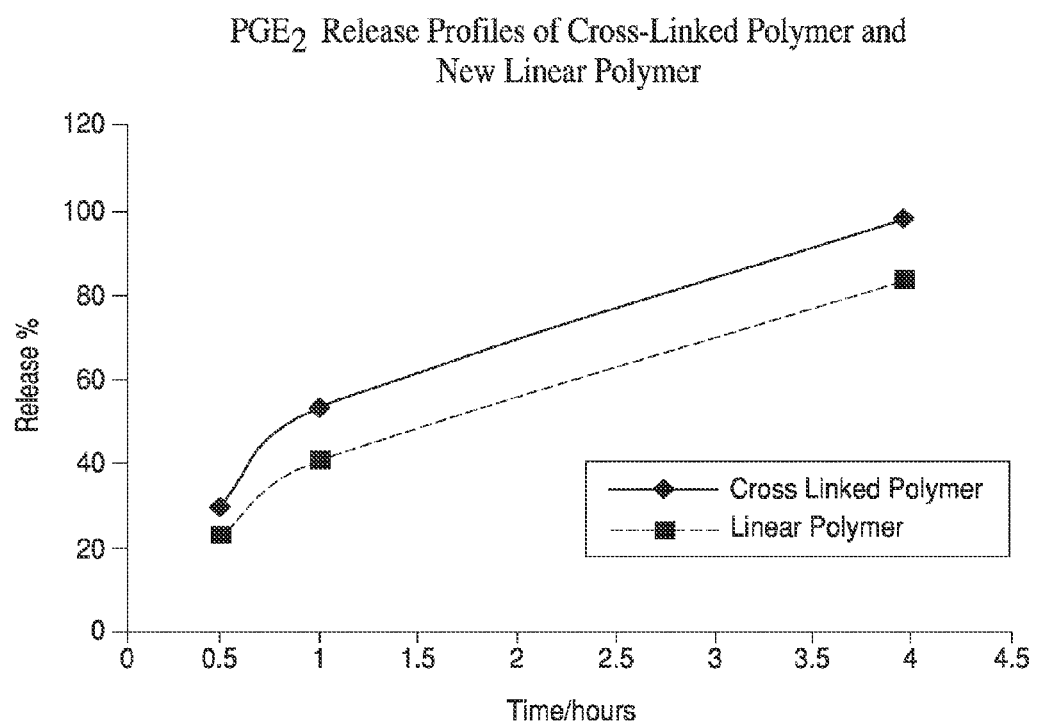
FIG. 4 graphically shows PGE2 release profiles of cross-linked polymer and new linear polymer.

FIG. 4 shows $PGE_2$ release profiles of cross-linked polymer and new linear polymer.

A4. Manufacture of Films

In initial experimentation into film manufacture, six vials were set up containing one, two, three, four, five and eight slices of polymer respectively. The polymer batch used was FX02141. To each vial around 10 mL of dichloromethane was added. All vials were sonicated until the polymer dissolved. The resultant solutions were poured onto a watchglass (20 cm diameter) and allowed to dry in a fume cupboard uncovered.

In further film development work, the amounts of polymer and solvent were weighed into a suitable glass container, which was then sealed and sonicated until the polymer dissolved. Some films were poured on a watchglass as before, whilst others were poured in a petri dish (8 cm diameter). To control the drying of the films, some solutions poured were covered with a 1 L glass beaker. Films were also manufactured using a doctor blade, with the solution being poured onto a glass plate in a fume cupboard and spread along the length of the plate.

TABLE 10

Initial Film Manufacture Results

| Number of Slices of FX02141 in 10 mL Dichloromethane (DCM) | Notes on Resultant Film |
| --- | --- |
| 1 | Lots of small air bubbles. 0.023 mm thick |
| 2 | Removed from glass too quickly and film was self adhesive and formed a clump of sticky polymer |
| 3 | Air bubbles present from shaking which leads to holes in film. Film opaque in colour. 0.083 mm thick |
| 4 | Smooth, opaque film; some air bubbles. Around 8 cm in diameter. 0.112 mm thick |
| 5 | Good film that looks uniform on one side but half was partially stuck together due to being removed from watchglass before it was fully dry. 0.133 mm thick |
| 8 | Very strong film; air bubbles a problem. Oval in shape - 7 cm by 5 cm. 0.354 mm thick |

The film made with five slices of polymer in solvent was swollen in demineralised water in a plastic petri dish. The swollen form of the film was found to be strong. The film was placed on a watchglass to dry. Once dried, the film regained its shape and strength.

TABLE 11

Films Manufactured Using Polymer Batch FX02141 Dissolved in Dichloromethane

| Vial | Weight FX02141 (g) | Weight DCM added (g) | % w/w Polymer in DCM | Details |
| --- | --- | --- | --- | --- |
| 1 | 0.8911 | 12.763 | 6.98 | Loaded with cresol red. |
| 2 | 0.9478 | 13.806 | 6.87 | Loaded with bromophenol blue |
| 3 | 0.7897 | 14.797 | 5.34 | Poured onto watchglass with another watchglass placed on top; film not uniform |
| 4 | 0.9238 | 10.661 | 8.67 | Poured onto watchglass; film used for swelling over time test |
| 5 | 0.9572 | 15.936 | 6.01 | Poured onto watchglass, covered with a 1 litre beaker; film uniform |
| 6 | 0.8679 | 13.899 | 6.24 | Poured into a glass petrie dish, covered with beaker; uniform film; film used for crystallinity testing; film brittle |
| 7 | 0.9751 | 15.286 | 6.38 | Poured in a glass petrie dish, covered with beaker; film brittle |
| 8 | 1.0680 | 11.193 | 9.54 | Made into a 53.20% w/w solution of ethanol in DCM/polymer mixture; didn't go into a film |
| 9 | 1.0618 | 13.335 | 7.96 | Loaded with bromophenol blue; film swollen |
| 10 | 0.8490 | 11.557 | 7.35 | Made into a 34.73% w/w solution of acetonitrile in DCM/polymer mixture; film brittle - opaque looking |
| 11 | 0.6528 | 10.029 | 6.51 | Made into a 45.00% w/w solution of methanol in DCM/polymer mixture |
| 12 | 0.9013 | 6.541 | 13.78 | Made into a 108% w/w solution of acetone in DCM/polymer mixture, poured onto watchglass and covered with beaker; film not uniform |

Portions of films made from Vials 1 and 2 were cut and placed into vials of demineralised water to determine whether the film could release the loaded dye.

TABLE 12

Films Manufactured Using Polymer Batch FX02158 in Different Solvents

| Vial | Weight FX02158 (g) | Weight Solvent Added (g) | % w/w Polymer in Solvent | Details |
|---|---|---|---|---|
| A | 0.7677 | 10.0211 g methanol | 7.66 | Non-uniform: one large clearer patch visible; feels smooth; opaque film; slightly textured looking |
| C | 0.7755 | 15.9041 g dichloromethane | 4.88 | Uniform in appearance; opaque film covered in small clear spots all over; feels rough; not brittle |
| E | 0.7631 | 9.6095 g dichloromethane and 4.9686 g methanol | 5.23 | Uniform film; smooth to touch; very brittle and breaks on touching; opaque film covered in clear spots which are smaller and more spread out than vial c |

The polymer in vials C and E began dissolving immediately, whereas vial A was slower. The solutions from these vials were poured into separate glass petri dishes in a fume cupboard and each covered with a one-liter beaker. They were left until dry. It was noticed that the solution from vial c dried quicker than that of vials a and e.

TABLE 13

Films Manufactured to Compare Drying Techniques

| Duran | Weight Polymer (g) | Weight DCM (g) | % w/w polymer in DCM |
|---|---|---|---|
| 1 | 1.9542 FX02158 | 37.2 | 5.25 |
| 2 | 1.9806 FX02158 | 35.6 | 5.56 |
| 3 | 1.8595 FX02144 | 40.0 | 4.65 |
| 4 | 1.8508 FX02144 | 37.0 | 5.00 |

The solutions from all four durans were poured separately into glass petri dishes in a fume cupboard.

Durans 1 and 3 were covered with a one-liter glass beaker, and durans 2 and 4 were left uncovered.

Films from durans 1 and 3 feel rough to touch, whereas films from durans 2 and 4 are smooth. Film from duran 2 has a rougher patch at one side.

All films manufactured from durans 1-4 were of comparable strength and none were brittle.

Two films were manufactured using the doctor blade. Both polymers used were dissolved in DCM (about 5% w/w) to make the solution, and both solutions were poured onto the same glass dish under the same conditions.

The film manufactured with polymer FX02144 was brittle and fell apart on storage whereas the film made with FX02158 (which was loaded with bromophenol blue for a demonstration) remained intact.

Figure 5:
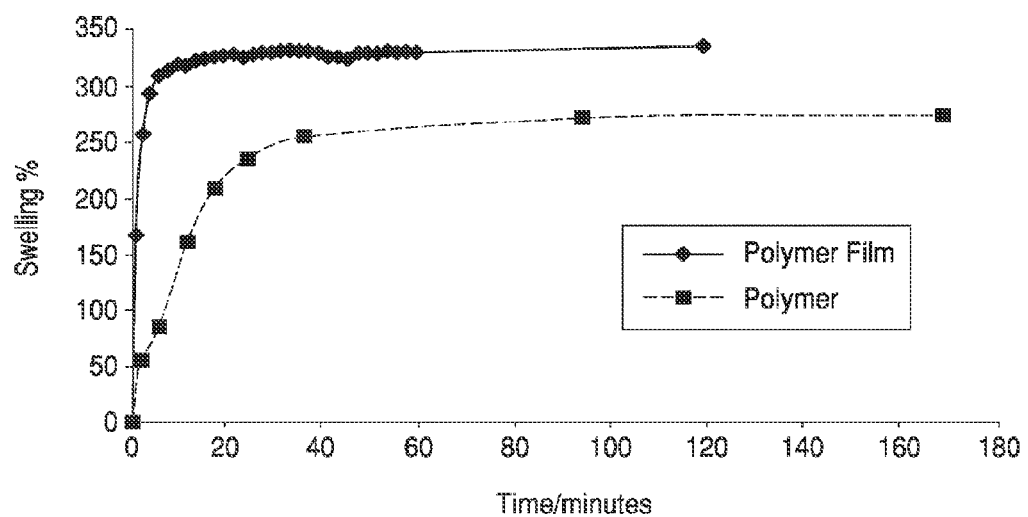
FIG. 5 graphically shows comparison of percentage swelling over time of polymer film.
Figure 6:
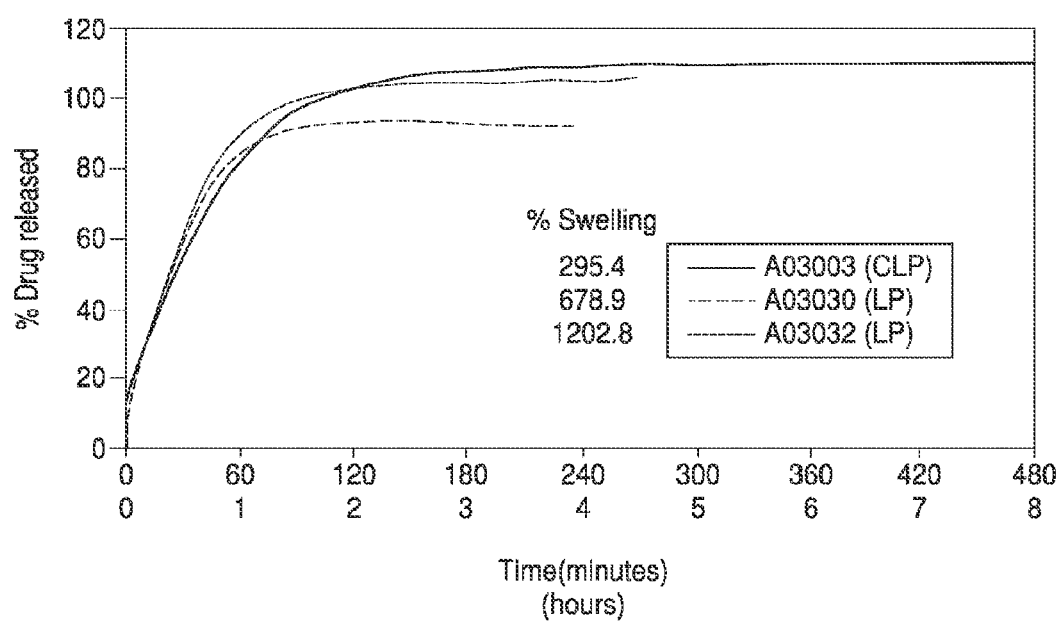
FIG. 6 graphically shows mean dissolution profile of clindamycin phosphate from various pessaries.
Figure 7:
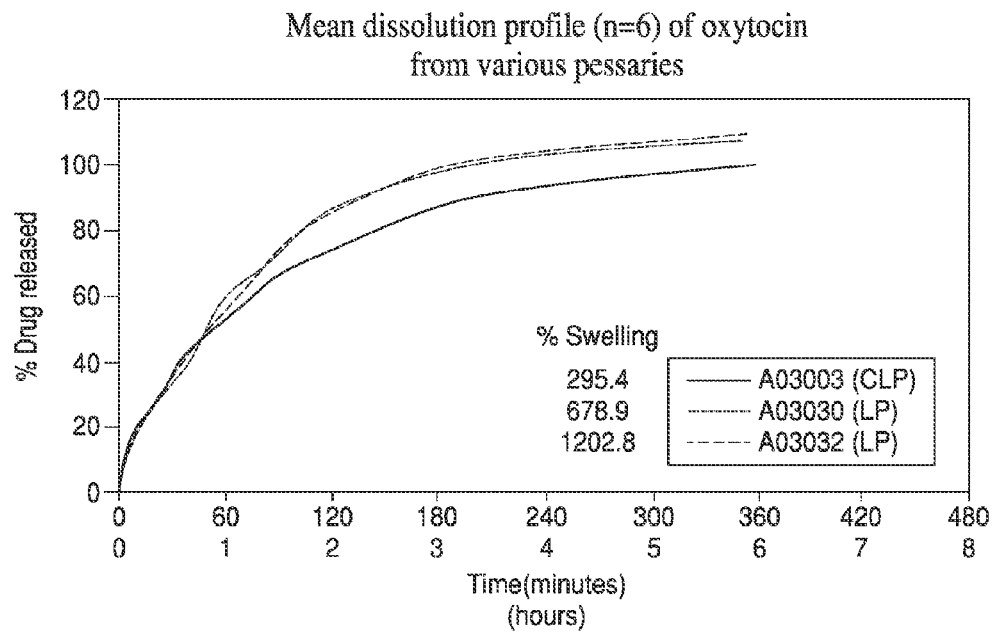
FIG. 7 graphically shows mean dissolution profile of oxytocin from various pessaries.
Figure 8:
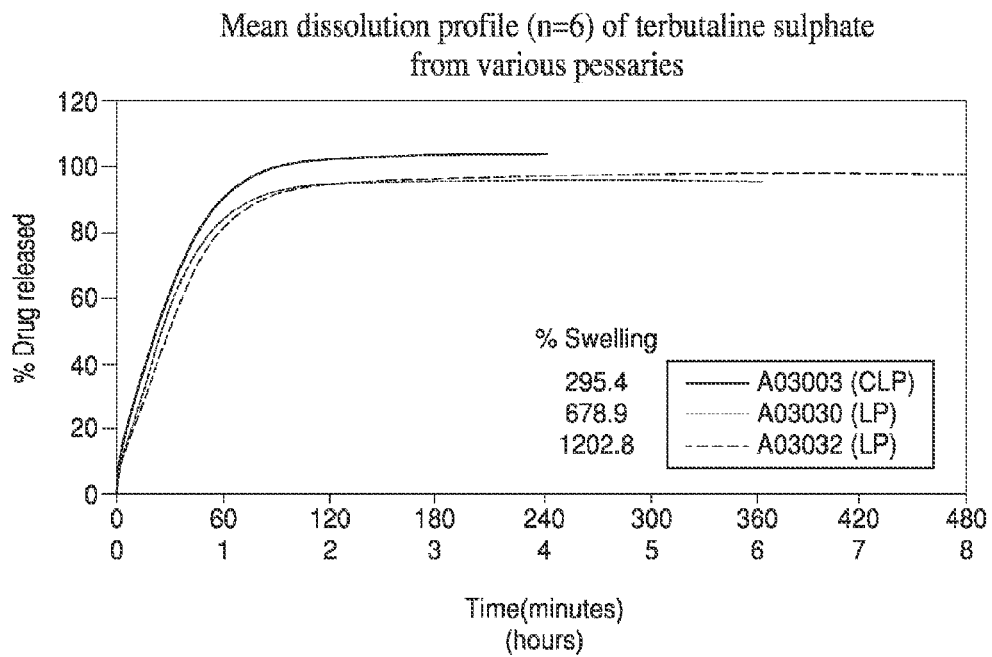
FIG. 8 graphically shows mean dissolution profile ofterbutaline sulphate from various pessaries.
Figure 9:
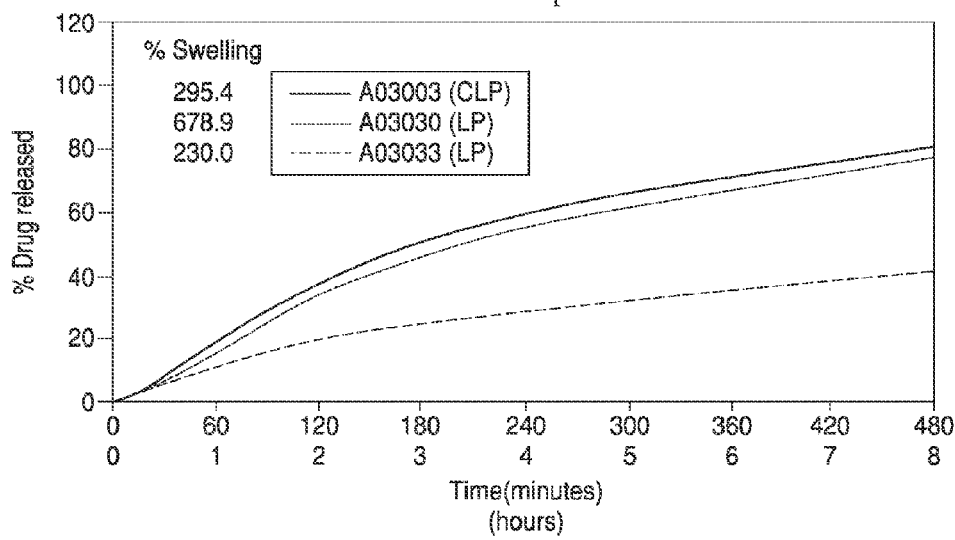
FIG. 9 graphically shows mean dissolution profile of misoprostol from various pessaries.
Figure 10:
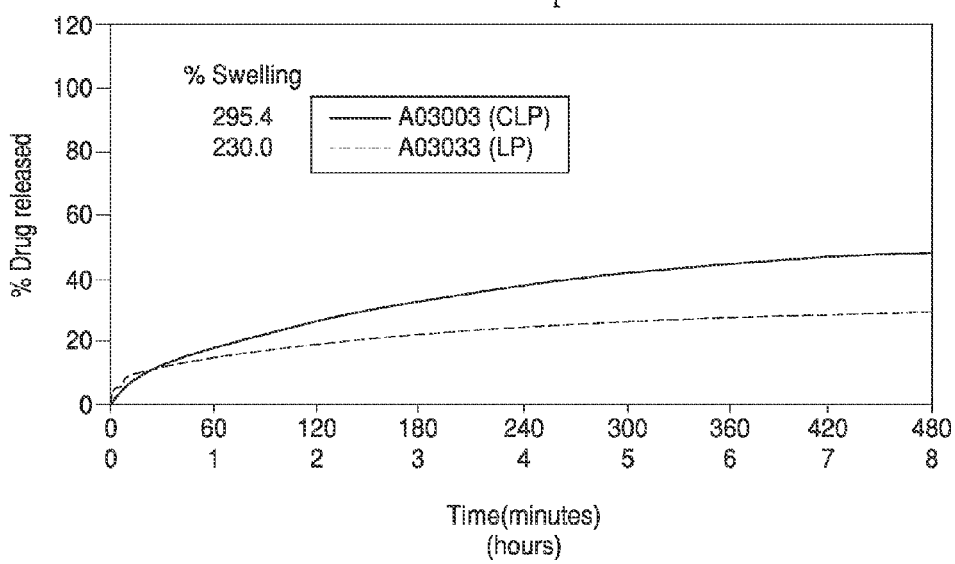
FIG. 10 graphically shows mean dissolution profile of progesterone from various pessaries.

To access the release of a drug from a polymer film, the percentage swelling over time was calculated. This was graphically represented, using the percentage swelling over time of the polymer slice of same batch used in film manufacture as a reference. The results are shown in FIG. 5.

The average weight of a film portion used was 0.0272 g; and the average weight of a polymer slice (FX02141) was 0.1381 g.

A5. Discussion a. Appearance

During appearance testing, it was observed that new linear polymer billets were slightly darker in colour when compared to known cross-linked polymer billets. This was accounted for by comparing the $FeCl_3$ content in both. It was calculated that known cross-linked polymer contained 0.01% w/w $FeCl_3$ in PEG whereas linear polymer had 0.0266% w/w $FeCl_3$ in PEG.

b. Cure Time

Previous linear polymers were manufactured with a 20 hour cure time, however batches FX02140 and FX02141 were manufactured with a 10 hour cure time.

By comparison of two batches with the same ingredient ratio but different cure times [FX02140 (10 hour cure time) and FX02143 (20 hour cure time)], it was seen that a cure time of 10 hours produced more promising results with a lower RSD for percentage swelling test and a lower percent water soluble extractables. As a result, a 10 hour cure time was then used for batches FX02144, FX02148 and FX02158.

However, the effect of cure time was further investigated using batches FX02141, FX02149 and FX02161 with cure time of 10, 20 and 30 hours respectively. By comparison of results from these three batches, it was found that there was no correlation in crystallinity; % WSE decreased as the cure time increased and the percentage swelling for FX02144 is about 20% less than the swellings of FX02149 and FX02161 which are identical. The RSD for percentage swelling decreased as cure time increased.

c. Ingredient Ratio

Polymer manufactured with a PEG:DD:DMDI ratio of 0.25:1:1.25 was shown to have the same characteristics as the cross-linked polymer, with all results within the known cross-linked polymer specifications.

The linear polymer according to the invention meets these specifications and the results are reproducible. Furthermore, the linear polymer is soluble in certain solvents whereas the known cross-linked polymer is insoluble.

The known cross-linked polymer, with a percentage swelling of around 300%, cannot be loaded with drugs of high molecular weight, such as peptides and proteins.

In comparison, a linear polymer of the present invention, FX02158 (PEG:DD:DMDI 0.7:1:1.7), was shown to have a percentage swelling of 730% and insoluble in water.

d. Swelling Profile

As the ratio of PEG:DD increased, the percentage swelling at 24 hours also increases. The accepted percentage swelling test for the known cross-linked polymers is 24 hours. This was extended to 72 and 144 hours for the polymer according to the invention to ascertain the time required for the polymer slice to reach maximum swelling.

With higher ratios of PEG:DD, it was found that the percentage swelling increased by a larger difference between 24 and 144 hours when compared to polymers with a low PEG:DD ratio. There was a 3% increase in percentage swelling of FX02141 (PEG:DD 0.25:1) from 24 to 144 hours compared to a 13% increase in FX02158 (PEG:DD: 0.7:1).

Polymers with higher PEG:DD ratios have not reach their maximum percentage swelling by 24 hours. This is confirmed by percentage swellings over time curves (FIG. 2). Polymer slices with a PEG:DD ratio of 0.25:1 reach their maximum swelling by around 5 hours when the curve plateaus, however, polymer slices with a higher PEG:DD ratio of 0.7:1 it was seen that the percentage swelling was increasing at 144 hours with the gradient of the curve at this point being positive.

e. Stability

Stability testing at 40° C. was carried out on FX02150 (purified FX02144) over a period of 4 weeks. The results have shown that the percentage swellings increased with time and this is comparable to results of cross-linked polymers at 40° C.

f. Drug Release

Polymer batch FX02144 (PEG:DD:DMDI 0.25:1:1.25) was loaded with pilocarpine and $PGE_2$. This polymer has similar characteristics to cross-linked polymer and therefore, release profiles of both drugs from the two different polymers could be compared.

The release characteristics of pilocarpine were shown to be comparable between linear and cross-linked polymer. This was confirmed by comparison of percentage swelling over time of the linear batch with cross-linked polymer (FIG. 1) where the rate of swelling was the same for both.

However, $PGE_2$ release was found to be different. The linear polymer released the drug slower than the cross-linked polymer.

g. Solubility Testing

Four different polymers, with different ingredient ratios, were manufactured and none of these polymers were soluble in ethanol or acetone.

FX02144 was insoluble in methanol, whereas other batches tested were soluble in this solvent.

All batches tested were soluble in dichloromethane.

h. Film Preparation

From initial experimentation a promising combination of polymer and solvent was found to be 4-5 slices (approx equivalent to 0.7 g polymer) in 10 mL DCM. This was scaled up to 13 slices in 30 mL DCM and the film manufacture was shown to be reproducible with similar films achieved using this combination.

A manufactured film was swollen in demineralised water and the swollen form was found to be strong and stretchy. This swollen film was then removed from the water and allowed to dry. Once dried, the film regained its shape and strength.

On further film development, the film was tested to determine whether it could release a loaded dye. Portions of films loaded with dye were submerged in water, and the water colour changed over time showing that the film had the ability to release a loaded substance.

It was discovered that a film manufactured by dissolving the polymer in different solvents had an effect on the total drying time of the film, the uniformity, texture and strength of the final film. In addition, the technique used to dry the films had an effect on its final appearance in terms of uniformity and texture.

The percentage swelling over time of a polymer film produced was calculated, and compared to the percentage swelling over time of the polymer slices used to make the film. As expected, the portions of film reached their maximum percentage swelling much quicker than the polymer slice because the thickness and average weight of the film portions were much less than the polymer slices. This can be used as an indication of release rate of a drug from a polymer film.

Section B

B1 Polymer Manufacture

Various type of polyethylene glycols, diols and diisocyanates, and various stoichiometric ratios of these compounds were used to further demonstrate their effects on the properties of the new polymer. PEG4000, PEG8000, PEG12000 and PEG35000 are polyethylene glycols having molecular weight of 4000, 8000, 12000 and 35000, respectively; HD is 1,6-hexanediol, DD is 1,10-decanediol, DDD is 1,12-dodecanediol and HDD is 1,16-hexadecanediol; DMDI is dicyclohexylmethane-4,4-diisocyanate and HMDI is 1,6-hexamethylene diisocyanate.

Polymers, except batch numbers BP03007, BP03014 and BP03015, were produced with the same polymerisation method as in Section A. The only difference was that the melted PEG and diol mixture was mixed for 30 minutes in a rotavapor, before 100 g was taken out to make a catalyst mixture to produce a more homogenous mixture.

For polymerisation of PEG35000 (batch numbers BP03007 and BP03014) the polymerisation reactor was changed to a stirring tank reactor (700 ml) and the polymerisation temperature was increased to 140° C. to reduce the melt viscosity of the PEG. PEG was dried overnight in a rotavapor using vacuum and 50° C. temperature. PEG, diol and ferric chloride were fed to a stirring tank glass reactor. The mixture was melted for 2 hours under nitrogen using a 140° C. oil bath. Mixing was turned on for 30 min before diisocyanate was fed to the reactor and then mixed for 5 min. Polymer was poured to the preheated mould (130° C.) and kept for 10 hours in an oven at 95° C. After this time, the oven was turned off and the polymer billets were left to cool to room temperature. The polymer billets were then demoulded and sliced.

A two-step polymerisation method was also used to produce more controlled polymer structure (batch number BP03015). PEG was dried overnight using vacuum and 50° C. in a rotavapor. Diisocyanate was first fed to the stirring tank reactor. Then about 40 g PEG with ferric chloride on the top of it was fed to the reactor. The reactor was heated to 95° C. and PEG was fed to the reactor during 3 hours by using about 20 g portions at the each time. Mixing (30 rpm) was turned on when the reactor temperature reached 95° C. Then the diol was fed to the reactor and mixing increased to 60 rpm and mixed for 5 min. Polymer was poured into the preheated mould (95° C.) and kept for 10 hours in an oven at 95° C. After this time, the oven was turned off and the polymer billets were left to cool to room temperature. The polymer billets were then demoulded and sliced.

B2. Polymer Properties

The effects of type and ratios of polyethylene glycols, diols and diisocyanates on the properties of polymers can be seen in Tables 14-18.

TABLE 14

Molar ratios between PEG 8000 and 1,10-decanediol was changed.

| | Batch Number | | | |
|---|---|---|---|---|
| | 03032 | 03030 | 03031 | 03033 |
| PEG 8 000 (Molar Ratio) | 0.9 | 0.7 | 0.7 | 0.1 |
| DD (Molar Ratio) | 1 | 1 | 1 | 1 |
| DMDI (Molar Ratio) | 1.9 | 1.7 | 1.7 | 1.1 |
| Cure Time | 10 | 10 | 10 | 10 |
| Percentage Swelling (%) | 1048 | 612 | 750 | 178 |

TABLE 14-continued

Molar ratios between PEG 8000 and 1,10-decanediol was changed.

| | Batch Number | | | |
|---|---|---|---|---|
| | 03032 | 03030 | 03031 | 03033 |
| WSE (%) | 2.3 | 1.0 | 1.4 | 2.3 |
| Tm (° C.) | 62.4 | 61.4 | 62.4 | 54.9 |
| Crystallinity (%) | 48.6 | 52.7 | 49.3 | 33.1 |
| Soluble in DCM | yes | yes | yes | yes |
| Soluble in THF | no | no | no | yes |

DD is 1,10-decanediol
DMDI is dicyclohexylmethane-4,4-diisocyanate
WSE is water soluble extractable

TABLE 15

The length of PEG was changed.

| | Batch Number | | | | |
|---|---|---|---|---|---|
| | Bp03001 | 03031 | BP03005 | BP03007 | BP03014 |
| PEG (MW) | 4 000 | 8 000 | 12 000 | 35 000 | 35 000 |
| PEG (Molar Ratio) | 0.7 | 0.7 | 0.7 | 0.7 | 0.1 |
| DD (Molar Ratio) | 1 | 1 | 1 | 1 | 1 |
| DMDI (Molar Ratio) | 1.7 | 1.7 | 1.7 | 1.7 | 1.1 |
| Cure time | 10 | 10 | 10 | 10 | 10 |
| Percentage Swelling (%) | 395 | 750 | 993 | Lost Integrity | 742 |
| WSE (%) | 1.3 | 1.4 | N.D. | WS | CH |
| Tm (° C.) | 53.8 | 62 | 64.0 | 65.7 | 65.3 |
| Crystallinity (%) | 36.3 | 49.3 | 46.5 | 64.7 | 46.4 |
| Soluble in DCM | yes | yes | yes | yes | yes |
| Soluble in THF | yes | no | no | no | no |

MW is molecular weight
DD is 1,10-decanediol
DMDI is dicyclohexylmethane-4,4-diisocyanate
WS water soluble
CH changes in shapes

TABLE 16

The length of diol and the amount of diol was changed.

| | Batch Number | | | | | |
|---|---|---|---|---|---|---|
| | 03035 | 03031 | Bp03002/1 | 03036 | 03034 | BP03006 |
| Diol | HD | DD | DDD | DDD | DDD | HDD |
| PEG 8 000 (molar ratio) | 0.7 | 0.7 | 1.5 | 0.9 | 0.7 | 0.7 |
| Diol (molar ratio) | 1 | 1 | 1 | 1 | 1 | 1 |
| DMDI (molar ratio) | 1.7 | 1.7 | 2.5 | 1.9 | 1.7 | 1.7 |
| Cure Time | 10 | 10 | 10 | 10 | 10 | 10 |
| Percentage Swelling (%) | 899 | 751 | 1679 | 602 | 640 | 470 |
| WSE (%) | 0.92 | 1.4 | 5.7 | 0.7 | 0.89 | N.D. |
| Tm (° C.) | 61.8 | 62 | 61.1 | 60 | 60.6 | 60.1 |
| Crystallinity (%) | 52.8 | 49.3 | 48.7 | 43.1 | 38.2 | 45.8 |
| Soluble in DCM | yes | yes | yes | yes | yes | yes |
| Soluble in THF | no | no | no | no | no | no |

HD is 1,6-hexanediol
DD is 1,10-decanediol
DDD is 1,12-dodecanediol
HDD is 1,16-hexadecanediol
DMDI is dicyclohexylmethane-4,4-diisocyanate

TABLE 17

The effect of diisocyanate.

| | Batch Number | |
|---|---|---|
| | 03032 | BP03003 |
| Diisocyanate | DMDI | HMDI |
| PEG 8 000 (molar ratio) | 0.7 | 0.7 |
| DD (molar ratio) | 1 | 1 |
| DMDI (molar ratio) | 1.7 | 1.7 |
| Cure Time | 10 | 10 |
| Percentage Swelling (%) | 751 | 1070 |
| WSE (%) | 1.4 | N.D. |
| Tm (° C.) | 62 | 63.4 |
| Crystallinity (%) | 49.3 | 52.2 |
| Soluble in DCM | yes | yes |
| Soluble in THF | no | no |

DMDI is dicyclohexylmethane-4,4-diisocyanate
HMDI is 1,6-hexamethylene diisocyanate

TABLE 18

Two-step Polymerisation method

| | Batch number BP03016 |
|---|---|
| PEG 8 000 (molar ratio) | 0.7 |
| DD (molar ratio) | 1 |
| DMDI (molar ratio) | 1.7 |
| Cure Time | 10 |
| Percentage Swelling (%) | 1750 |
| WSE (%) | N.D. |
| Tm (° C.) | 61.2 |
| Crystallinity (%) | 52.4 |
| Soluble in DCM | yes |
| Soluble in THF | no |

DD is 1,10-decanediol
DMDI is dicyclohexylmethane-4,4-diisocyanate

B3 Controlled Release Compositions
Linear Polymer Characterisation & Drug Loading Examples Batches of linear polymer (03030, 03032 and 03033), together with cross-linked polymer batch 03003 (polymer ratio PEG 8000:hexanetriol:DMDI of 1.0:1.2:2.8) for comparison were sliced to produce polymer slices of dimension 10 mm×30 mm×1.0 mm. The polymer slices were purified at 25° C. using three washes in purified water and/or purified water/ethanol. Next, all slices were dried under vacuum.

Five drugs namely clindamycin phosphate, oxytocin, terbutaline sulphate, misoprostol and progesterone were loaded into the various polymers. These drugs were chosen as they covered various aspects such as highly water soluble, poorly water soluble, peptides, steroids and lower molecular weight molecules.

The drugs were loaded into the polymer by dissolving each drug candidate into a suitable solution, immersing the polymer slices for an appropriate time then removing from the solution and drying. Table 19 details the loading parameter and conditions.

TABLE 19

Loading parameters for various drug candidates

| | Drug | | | | |
|---|---|---|---|---|---|
| | CLI | OXY | TBS | MIS | PRO |
| General Batch no. | | | | | |
| A03003 (CLP) | CL 03009 | OX 03001 | FX 02248 | MS 03025 | PG 03002 |
| A03030 (LP) | CL 03017 | OX 03002 | TB 03001 | MS 03030 | — |
| A03032 (LP) | CL 03020 | OX 03003 | TB 03002 | — | — |
| A03033 (LP) | — | — | — | MS 03033 | PG 03003 |
| Drug content/unit | 70 mg | 1 mg | 10 mg | 200 µg | 10 mg |
| Drug solubility (in water) | Very soluble (500 mg/ml) | Very soluble | Soluble (250 mg/ml) | Insoluble (3 mg/ml) | Insoluble (<0.4 mg/ml) |
| No. of pessary (n) | 18-23 | 18-23 | 18-23 | 18-23 | 18-23 |
| Loading | | | | | |
| Loading solution | 4.76% w/w NaCl solution | PBS solution (pH 7.4) | Purified water | 25% w/w EtOH solution | 75% w/w EtOH solution |
| Loading temperature | 25° C. | 25° C. | 25° C. | 4° C. | 25° C. |
| Incubation | | | | | |
| Incubation temperature | 25° C. | 25° C. | 25° C. | 4° C. | 25° C. |
| Incubation duration | 16-24 hours | 16-24 hours | 16-24 hours | 16-24 hours | 16-24 hours |
| Drying | | | | | |
| Drying method | Vacuum oven | Vacuum oven | Vacuum oven | Vacuum oven | Rotavapor |
| Drying temperature | Room temperature | Room temperature | Room temperature | Room temperature | Room temperature |
| Drying duration | ≥72 hours (as required) | ≥24 hours (as required) | ≥24 hours (as required) | ≥24 hours (as required) | ≥24 hours (as required) |

Abbreviations:
CLI—Clindamycin phosphate; OXY—Oxytocin; TBS—Terbutaline sulphate; MIS—Misoprostol; PRO—Progesterone; NaCl—Sodium chloride; PBS—Phosphate buffered saline; EtOH—Ethanol The drug loaded polymer were analysed for in vitro drug release following USP Method XXIII, Apparatus 2 at 37° C., with 50 rpm paddle speed. Drug release was analysed by ultraviolet spectroscopy or high pressure liquid chromatography (HPLC) as appropriate. Various dissolution parameters or settings are summarised in Table 20.

TABLE 20

Dissolution parameters and settings

| | Drug | | | | |
|---|---|---|---|---|---|
| | CLI | OXY | TBS | MIS | PRO |
| Dose per unit (mg) | 70 | 1 | 10 | 0.2 | 10 |
| Dissolution volume, V (ml) | 900 | 100 | 250 | 250 ml | 900 |
| Dissolution media | Water | Phosphate buffer solution (pH 7.4) | Water | Water | Water |
| Wavelength, λ (nm) | 210 | 562 | 276 | 280 (after derivitisation) | 249 |

Abbreviations;
CLI—Clindamycin phosphate;
OXY—Oxytocin;
TBS—Terbutaline sulphate;
MIS—Misoporstol;
PRO—Progesterone;
NA—Not available FIGS. 6 to 10 show the mean dissolution profiles of each drug candidate from the various polymers.

Figure 11:
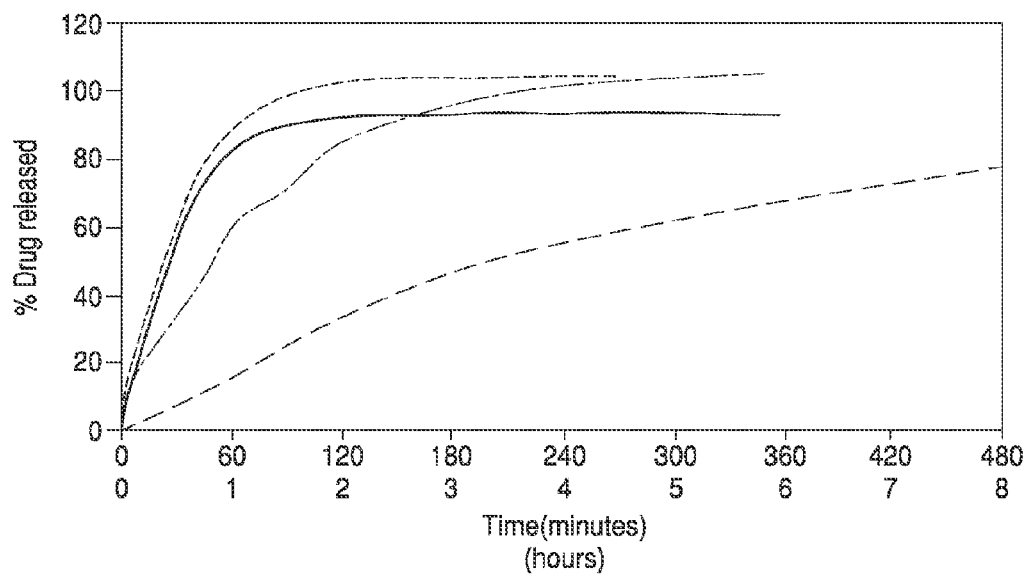
FIG. 11 graphically shows mean dissolution profile of various drug candidates from linear polymer pessaries.

The effect of drug type on mean dissolution profile of linear polymer batch A03030 is shown in FIG. 11.

Rate of drug release k values of each dissolution profile was determined by calculating the slope of graph % drug release versus square root time. All the linear relationship between % drug release and square root time has $R^2$ correlation value >0.95%. Rate of drug release k from the dissolution profiles of each drug candidate from various pessaries are shown in Table 21.

TABLE 21

Rate of drug release (k minutes$^{-1/2}$) of drug candidates from cross-linked and linear polymer pessaries

| | | Drug Polymer type | Rate of drug release, k (minute$^{-0.5}$) | | | |
|---|---|---|---|---|---|---|
| Water solubility (mg/ml) | Molecular weight | % Swelling (in water) | | A03003 (CLP) 295.4 | A03033 (LP) 230.0 | A03030 (LP) 678.9 | A03032 (LP) 1202.8 |
| 500 | 505 | CLI | 10.701 | -ND- | 12.765 | 12.380 |
| Very soluble | 1007 | OXY | 6.749 | -ND- | 7.875 | 7.85 |
| 250 | 274 | TBS | 13.628 | -ND- | 13.262 | 11.954 |
| 3 | 383 | MIS | 4.507 | 2.213 | 4.378 | -ND- |
| <0.4 | 315 | PRO | 2.414 | 1.256 | -ND- | -ND- |

Abbreviations:
CLI—Clindamycin phosphate;
OXY—Oxytocin;
TBS—Terbutaline sulphate;
MIS—Misoporstol;
PRO—Progesterone;
CLP—Cross-linked polymer;
LP—Linear polymer;
ND—No data

The invention claimed is:
1. A controlled release composition, comprising a cross-linked polyurethane polymer loaded with misoprostol;

wherein the cross-linked polyurethane polymer is formed from a polyethylene glycol, a triol and a diisocyanate, and at least about 80% of the misoprostol is released when the composition is immersed in water at 37° C. for 480 minutes.

2. The composition of claim 1, wherein the cross-linked polyurethane polymer is formed from PEG8000, hexanetriol and dicyclohexylmethane-4.4-diisocyanate.

3. The composition of claim 2, wherein the ratio of PEG8000:hexanetriol:dicyclohexylmethane-4.4-diisocyanate is in the range of 0.8-1.0:1.0-1.2:2.3-2.8.

4. The composition of claim 3, wherein the ratio of PEG8000:hexanetriol:dicyclohexylmethane-4.4-diisocyanate is 1.0:1.2:2.8.

5. The composition of claim 3, wherein the ratio of PEG8000:hexanetriol:dicyclohexylmethane-4.4-diisocyanate is 0.8:1.0:2.3.

6. The composition of claim 1, wherein the misoprostol content is 200 μg.

7. The composition of claim 1, wherein the composition is in the form of a pessary.

8. The composition of claim 7, wherein the composition has been dried in a vacuum oven at room temperature for at least 24 hours.

9. The composition of claim 7, wherein the composition has a misoprostol release rate of 4.507 minute$^{-0.5}$.

10. The composition of claim 1, wherein the polyurethane polymer has a swellability of about 295%.

\* \* \* \* \*